US007067722B2

(12) United States Patent
Fillatti

(10) Patent No.: US 7,067,722 B2
(45) Date of Patent: Jun. 27, 2006

(54) NUCLEIC ACID SEQUENCES AND METHODS OF USE FOR THE PRODUCTION OF PLANTS WITH MODIFIED POLYUNSATURATED FATTY ACIDS

(75) Inventor: JoAnne J. Fillatti, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 341 days.

(21) Appl. No.: 10/176,149

(22) Filed: Jun. 21, 2002

(65) Prior Publication Data

US 2003/0172399 A1    Sep. 11, 2003

Related U.S. Application Data

(63) Continuation-in-part of application No. 09/638,508, filed on Aug. 11, 2000, now abandoned.

(60) Provisional application No. 60/151,224, filed on Aug. 26, 1999, provisional application No. 60/172,128, filed on Dec. 17, 1999.

(51) Int. Cl.
*A01H 5/04* (2006.01)
(52) U.S. Cl. .................................. 800/312; 800/281
(58) Field of Classification Search ................ 800/281, 800/312
See application file for complete search history.

(56) References Cited

U.S. PATENT DOCUMENTS

| | | | |
|---|---|---|---|
| 4,557,734 A | 12/1985 | Schwab et al. |
| 5,454,842 A | 10/1995 | Poirier et al. |
| 5,475,099 A | 12/1995 | Knauf et al. |
| 5,627,061 A | 5/1997 | Barry et al. |
| 5,633,435 A | 5/1997 | Barry et al. |
| 5,714,670 A | 2/1998 | Fehr et al. |
| 5,723,595 A | 3/1998 | Thompson et al. |
| 5,723,761 A | 3/1998 | Voelker et al. |
| 5,850,026 A | 12/1998 | DeBonte et al. |
| 5,888,947 A | 3/1999 | Lambert et al. |
| 5,891,203 A | 4/1999 | Ball et al. |
| 5,955,329 A | 9/1999 | Yuan et al. |
| 5,955,650 A | 9/1999 | Hitz |
| 6,013,114 A | 1/2000 | Hille et al. |
| 6,331,664 B1 | 12/2001 | Rubin-Wilson et al. |
| 2003/0049835 A1 | 3/2003 | Helliwell et al. |
| 2003/0135882 A1 | 7/2003 | Metzlaff et al. |
| 2004/0107460 A1 | 6/2004 | Fillatti et al. |
| 2004/0126845 A1 | 7/2004 | Eenennaam et al. |
| 2005/0034190 A9 | 2/2005 | Fillatti et al. |

FOREIGN PATENT DOCUMENTS

| | | |
|---|---|---|
| EP | 0 959 133 A1 | 11/1999 |
| WO | WO 93/11245 | 6/1993 |
| WO | WO 94/10189 A1 | 5/1994 |
| WO | WO 94/11516 | 5/1994 |
| WO | WO 98/05770 A2 | 2/1998 |
| WO | WO 98/30083 | 7/1998 |
| WO | WO 98/46776 A2 | 10/1998 |
| WO | WO 98/53083 A1 | 11/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 00/07432 A1 | 2/2000 |
| WO | WO 00/44895 A1 | 8/2000 |
| WO | WO 00/44914 A1 | 8/2000 |
| WO | WO 00/68374 A1 | 11/2000 |
| WO | WO 02/04581 A1 | 1/2001 |
| WO | WO 01/14538 A2 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/15675 A1 | 2/2002 |
| WO | WO 03/080802 A2 | 10/2003 |

OTHER PUBLICATIONS

Lee et al, Plant Physiology 119: 989-1000, 1999.*
Cartea, M.E., et al., "Comparison of Sense and Antisense Methodologies for Modifying the Fatty Acid Composition of *Arabidopsis Thaliana* Oilseed", *Plant Science*,136:181-194 (1998).
Clark-Walker, G.D., et al., "Location of Transcriptional Control Signals and Transfer RNA Sequences in *Torulopsis-Glabrata* Mitochondrial DNA," *EMBO Journal*, 4:2, pp. 465-473, (1985).
EMBL Accession No. AB022220, "*Arabidopsis thaliana* DNA, chromosome 3, P1 clone: MLN21" (Jan. 1999).

(Continued)

*Primary Examiner*—Elizabeth F. McElwain
(74) *Attorney, Agent, or Firm*—Gary M. Bond; Chunping Li; Arnold & Porter LLP

(57) ABSTRACT

The present invention is directed to nucleic acid molecules and nucleic acid constructs, and other agents associated with fatty acid synthesis, particularly the ratios of saturated and unsaturated fats. Moreover, the present invention is directed to plants incorporating such agents where the plants exhibit altered ratios of saturated and unsaturated fats. In particular, the present invention is directed to plants incorporating such agents where the plants exhibit altered ratios of monounsaturated to polyunsaturated fatty acids.

13 Claims, No Drawings

OTHER PUBLICATIONS

EMBL Accession No. AB026636, "*Arabidopsis thaliana* genomic DNA, chromosome 3, TAC clone:K14A17" (May 1999).

EMBL Accession No. AC004705, "*Arabidopsis thaliana* chromosome 2 clone F26C24 map mi398, complete sequence" (May 1998).

EMBL Accession No. AL105179, "Drosophila melanogaster genome survey sequence T7 and of BAC BACN13A12 of DrosBAC library from Drosophila melanogaster (fruit fly)" (Jul. 1999).

EMBL Accession No. AL071390, "Drosophila melanogaster genome survey sequence TET3 end of BAC: BACR32M05 of RPCI-98 library from Drosophila melanogaster (fruit fly)" (May 1999).

EMBL Accession No. AL161581, "*Arabidopsis thaliana* DNA chromosome 4, contig fragment No. 77" (Mar. 2000).

EMBL Accession No. AL069706, "Drosophila melanogaster genome survey sequence T7 end of BAC: BACR29B23 of RPCI-98 library from Drosophila melanogaster (fruit fly)" (May 1999).

EMBL Accession No. AL108811, "Drosophila melanogaster genome survey sequence SP6 end of BAC BACN37D10 of DrosBAC library from Drosophila melanogaster (fruit fly)" (Jul. 1999).

EMBL Accession No. AL063932, "Drosophila melanogaster genome survey sequence TET3 end of BAC #BACR08O10 of RPCI-98 library from Drosophila melanogaster (fruit fly)" (May 1999).

EMBL Accession No. AW397948, "sg70c08.yl Gm-c1007 Glycine max cDNA clone genome systems clone ID: Gm-c1007-1767 5' similar to SW:FD61_SOYBN P48630 OMEGA-6 fatty acid desaturase, endoplasmic reticulum isozyme 1; mRNA sequence" (Feb. 2000).

European Patent Office, International Search Report, PCT/US00/22613 (mailed Apr. 26, 2001).

Okuley, John, et al., "Arabidopsis FAD2 Gene Encodes the Enzyme that is Essential for Polyunsaturated Lipid Synthesis", *The Plant Cell*, 6:147-158 (Jan. 1994).

Lewin, Benjamin M., "How did interrupted genes evolve," *Genes* (second edition), pp. 333-337 (1983).

Liu, Qing, Thesis, University of Sydney, Australia, pp. ii-iv, 24-26, 121-123, 142, 167, 168, 172-174, 179-181 (Mar. 1998).

Bouchon, P. et al., "Oil Distribution in Fried Potatoes Monitored by Infrared Microspectroscopy", *Journal of Food Science*, 66(7):918-923 (2001).

Buhr, T. et al., "Ribozyme Termination of RNA Transcripts Down-Regulate Seed Fatty Acid Genes in Transgenic Soybean", *The Plant Journal*, 30(2):155-163 (2002).

Cogoni, C. et al., "Post-Transcriptional Gene Silencing Across Kingdoms", *Curr. Opin. Gen. & Devel.*, 10(6):638-643 (2000).

Crossway, A. et al., "Integration of Foreign DNA Following Microinjection of Tobacco Mesophyll Protoplasts", *Mol. Gen. Genet.*, 202(2):179-185 (1986).

Dörmann, P. et al., "Accumulation of Palmitate in Arabidopsis Mediated by the Acyl-Acyl Carrier Proteini Thloesterase FATBl", *Plant Physiology*, 123:637-643 (2000).

Duffield, J. et al., "U.S. Biodiesel Development: New Markets for Conventional and Genetically Modified Agricultural Products", *Economic Research Service USDA*, pp. 1-31 (1998).

Dunn, R. et al., "Recent Advances in the Development of Alternative Diesel Fuel from Vegetable Oils and Animal Fats", *Recent Res. Devel. in Oil Chem.*, 1:31-56 (1997).

Ethan, S. et al., "Lubricant Basestocks from Vegetable Oils", *Industrial Crops and Products*, 11:277-282 (2000).

Fire, A. et al., "Potent and Specific Genetic Interference by Double-Stranded RNA in *Caenorhabditis elegans*", *Nature*, 391:806-811 (1998).

Halpin, C. et al., "Enabling Technologies for Manipulating Multiple Genes on Complex Pathways", *Plant Molecular Biology*, 47:295-310 (2001).

Hamada, T. et al., "Modification of Fatty Acid Composition by Over- and Antisense-Expression of a Microsomal $\omega$-3 Fatty Acid Desaturase Gene in Transgenic Tobacco", *Transgenic Research*, 5(2), 115-121 (1996).

Matzke, M.A. et al., "RNA-Based Silencing Strategies in Plants", *Curr. Opin. Gen. & Devel.*, 11(2):221-227 (2001).

Mensink, R. et al., "Effect of Dietary Fatty Acids on Serum Lipids and Lipoproteins: A Meta-Analysis of 27 Trials", *Arteriosclerosis and Thrombosis*, 12(8):911-919 (1992).

Montgomery, M.K. et al., "RNA as a Target of Double-Stranded RNA-Mediated Genetic Interference in *Caenorhabditis elegans*", *Proc. Natl. Acad. Sci. USA*, 95(96):15502-15507 (1998).

Napoli, C. et al., "Introduction of a Chimeric Chalcone Synthase Gene into Petunia Results in Reversible Co-Suppression of Homologous Genes *in trans*", *The Plant Cell*, 2:279-289 (1990).

Neff, W.E., et al., "Odor Significance of Undersirable Degradation Compounds in Heated Triolein and Trilinolein" *JAOC*, 77(12):1303-1313 (2000).

Sharp, P.A., "RNAi and Double-Strand RNA", *Genes & Development*, 13:139-141 (1999).

Sharp, P.A., "RNA Interference—2001", *Genes & Development*, 15:485-490 (2001).

Supplemental European Search Report in European Application No. 03711656.3 completed Jun. 29, 2005.

Timmons, J.S. et al., "Relationships Among Dietary Roasted Soybeans, Milk Components, and Spontaneous Oxidized Flavor of Milk", *Journal of Diary Science*, 84(11):2440-2449 (2001).

Toborek, M. et al., "Unsaturated Fatty Acids Selectively Induce an Inflammatory Environment in Human Endothelial Cells", *American Journal of Clin.l Nut.*, 75:119-125 (2002).

van der Krol, K.R. et al., "Flavonoid Genes in Petunia: Addition of a Limited Number of Gene Copies May Lead to a Suppression of Gene Expression", *The Plant Cell*, 2:291-299 (1990).

Warner, K. et al., "Effect of Oleic and Linoleic Acids on the Production of Deep-Fried Odor in Heated Triolein and Trilinolein", *Journal of Agricultural Food Chemical*, 49:899-905 (2001).

Waterhouse, P.M. et al., "Virus Resistance and Gene Silencing in Plants Can be Induced by Simultaneous Expression of Sense and Antisense RNA", *Proc. Natl. Acad. Sci. USA*, 95:13959-13964 (1998).

Wesley, S.V. et al., "Construct Design for Efficient, Effective and High-Throughput Gene Silencing in Plants", *The Plant Journal*, 27(6):581-590 (2001).

EMBL Accession No. AL069706, "Drosophila melanogaster genome survey sequence T7 end of BAC: BACR29B23 of RPCI-98 library from Drosophila melanogaster (fruit fly)"(May 1999).

EMBL Accession No. AL108811, "Drosophila melanogaster genome survey sequence SP6 end of BACBACN37D10 of DrosBAC library from Drosophila melanogaster (fruit fly)"(Jul. 1999).

EMBL Accession No. AL063932, "Drosophila melanogaster genome survey sequence TET3 end of BAC #BACR08O10 of RPCI-98 library from Drosophila melanogaster (fruit fly)"(May 1999).

EMBL Accession No. AW397948, "sg70c08.y1 Gm-c1007 Glycine max cDNA clone genome systems clone ID: Gm-c1007-1767 5'similar to SW:FD61_ SOYBN P48630 OMEGA-6 fatty acid desaturase, endoplasmic reticulum isozyme 1;, mRNA sequence"(Feb. 2000).

European Patent Office, International Search Report, PCT/US00/22613 (mailed Apr. 26, 2001).

Okuley, John, et al., "Arabidopsis FAD2 Gene Encodes the Enzyme that is Essential for Polyunsaturated Lipid Synthesis", *The Plant Cell*, 6:147-158 (Jan. 1994).

* cited by examiner

SEQUENCE LISTING

```
<160> NUMBER OF SEQ ID NOS: 39

<210> SEQ ID NO 1
<211> LENGTH: 420
<212> TYPE: DNA
<213> ORGANISM: Glycine max

<400> SEQUENCE: 1
gtaaattaaa ttgtgcctgc acctcgggat atttcatgtg gggttcatca tatttgttga      60
ggaaaagaaa ctcccgaaat tgaattatgc atttatatat cctttttcat ttctagattt     120
cctgaaggct taggtgtagg cacctagcta gtagctacaa tatcagcact tctctctatt     180
gataaacaat tggctgtaat gccgcagtag aggacgatca caacatttcg tgctggttac     240
tttttgtttt atggtcatga tttcactctc tctaatctct ccattcattt tgtagttgtc     300
attatcttta gattttttcac tacctggttt aaaattgagg gattgtagtt ctgttggtac     360
atattacaca ttcagcaaaa caactgaaac tcaactgaac ttgtttatac tttgacacag     420

<210> SEQ ID NO 2
<211> LENGTH: 405
<212> TYPE: DNA
<213> ORGANISM: Glycine max

<400> SEQUENCE: 2
gtatgatgct aaattaaatt gtgcctgcac cccaggatat ttcatgtggg attcatcatt      60
tattgaggaa aactctccaa attgaatcgt gcatttatat tttttttcca tttctagatt     120
tcttgaaggc ttatggtata ggcacctaca attatcagca cttctctcta ttgataaaca     180
attggctgta ataccacagt agagaacgat cacaacattt tgtgctggtt acctttttgtt     240 ttatggtcat gatttcactc tctctaatct gtcacttccc tccattcatt ttgtacttct     300 catattttc acttcctggt tgaaaattgt agttctcttg gtacatacta gtattagaca     360
ttcagcaaca acaactgaac tgaacttctt tatactttga cacag                     405

<210> SEQ ID NO 3
<211> LENGTH: 6220
<212> TYPE: DNA
<213> ORGANISM: Glycine max

<400> SEQUENCE: 3
agcttggtac cgagctcgga tccactagta acggccgcca gtgtgctgga attcggcttc      60
tctctcaccc tcctcttcac acattttctg tgcgctctaa caaacattct cgttcacact     120
ttcaggtact tttctctcct tatctcttta tctttattct ttcctacttt attgcttaaa     180
ccaatgctat ctatgcttcg atctcgcctt cttattttcc acttcccttt tctcgcttga     240
tctaaccgtt ttcgccctcc gcgcttcgat tgactgagta catctacgat tctctgttct     300
ttcatttcat agatttcgtc tgattttggc taacttggtt tctgttgcgg ccgattctta     360
```

-continued

```
catatactga ttgtttagca taaatgaact tgcttgttta gcactatctg catattttcg    420
tcacgcatct ctttcggatc taaggatgaa tctcctattt cctccgtatt atttctcgta    480
tctcttgttc tgtgctaatg ctccagaaaa tggcagcatt gtcttcttct ttgctgtata    540
agtgtttgtg ttgtgaatct ggaagcgatt ttgcgtgagg taacttgcga cttcaactat    600
tatctttcag atctcgttaa tttattagct gctattaatt tgtgtgtgca gtgtcaaact    660
gaagcacacg actgcttaga agttagaatt tgactgactg ttcctctttg atttttttct    720
ttctttcttt tgctwactcg gcctatttaa tgatctttat aaatagatta gtggaccact    780
tggttagttg gtgagttatg aatattcgaa ttttctacca caagttgggt taaaaaaatc    840
tctgcaacta cacgaggatt ttttatttta tttagaggaa actattctgt catccttttt    900
ccgattacac ttttctatca gttgttttga aatatacacc ttaggaatat aatattaccc    960
ctttcggtct aatataaat atattttaat tatttatatt ttatttaatg aaattatttt    1020
taaaatactt tcatttaata gaatttttaa taaagttaaa acttttatt gtgtagagtt    1080
taacgaagtt aattagtttt cttagtaaat gtaaatatg ccttttttgt tgtttataat    1140
ggagattgga aaaatatac tttaattttt ttcaagtgat gaataattat ggatgttttg    1200
tcaatatttt tgtcttgcta tacaactttc agtcttgcca ttaaataatt ttgaatgtgt    1260
tattgatatc tctgaacaat atttagagac gaacataaat tttatatatt ttatataatt    1320
tcttttatt accctttat tatcaatttt gaaatttggt taatatctgt gtttcatttt    1380
gaggtctcaa atttgatata aggaggttca aaatgcgttg ctagccattt taaagattag    1440
caggagagga aatgtttctg gacttaaatt taaaatatgc ttatttgttt ttcaagagag    1500
agagatcaat atttatataa tacacttgaa ttaatataca ccattgttgc aaaaaaaaaa    1560
aaatattagt tgattgtgtg acaatatttt atattaaata taattagtta atttagttca    1620
agttgagtta catttttaca taccattctt agccgccact ttttatatt tatttgtagg    1680
aataactttt catctgtatc aatttttcccc gtctaataaa aagggtttga cttttttctta    1740
taatagagtt tttttttttt tgctttaagt tattgtaaaa taattatttt attttttttg    1800
cctttgtaaa ttatgtatat ttaatgtttt aataggaaaa aaatgttatc aaaagcacta    1860
aaagactaaa attaaacaac cataatttgc aaagatgaaa ataaaaaaat aattttgtaa    1920
agataaaaaa tgaaataaaa tagttaaatt ataggaattt aaaagctatt taaatcaaca    1980
aaagttaaag tttctgtaaa aaagttcaa ttttttttt tattattgaa aaagttaaag    2040
ctaatgagcg ttcgatttgg gttagtatgt agtatttatt attttcaaga ttttggattt    2100
tattgtcgat gtttctgatt tgaatataat tattttccat tcaacttgtg attttataag    2160
aaaaaaaag gtacagaaaa aatcaagcgc ttttttttatt tcaattagtg gaggtttcac    2220
tgaaatgggt aaagaatcta ttttgcaatc acaattatta ccggtattca actgcaacaa    2280
ggaacaaaat tcctttcgta aatatacgga gaggaatcta ttttgacttg ttgaatttat    2340
ggtaaagtag aatttagaat ttaattatga gttgaagtaa ttttgaataa tttatatgtt    2400
aaatataaaa ttttgtacta agttttattc ataactttga ttctataata caaacataca    2460
taagttcaaa ataattttta attaaaatta attttatcaa ttttttattca aacacgagtc    2520
taatttgctt gatgaattaa gaaataagg aagaaaatat taaaaactag gagagaagtt    2580
aaagagaatt tcatctttat tattctcagt tgtttcaaaa ataatgaaag gatagctata    2640
taatactgta actgagccaa gaacatattt gccgtccgag taaccttttc ttttcttgtt    2700
ccgttttctc cgccgatgaa gagagggaag ggaatgtatc tttgtattta tgttttcaaa    2760
```

```
gagttcgtgc ataaaattgg tttaatcaaa tttttcataa gattattatt ttatgatttt    2820
ttaaaataaa ttagtaacta tattccgtaa gtcgtacaca gttatatgta gtaagtaaat    2880
tatattttaa taattattat cttaaaattt tcttaagaac ttggttaaaa tattttgtt     2940 tgaaaaagtt tatgataact tttttttgtt gaaaaaagt ttacgattat ctaactcgta     3000
cttagattat ttctaattgg gatttattga agggtttttt aagtaaagaa attgtttctt    3060
atggtttctt ttttattgga caaatttacg tagcaaagag tgtttcttaa aaacaagaca    3120
tgtatccttt gaaaaaaaac tatttctttg aaataaaaaa taatatttat ctggcacata    3180
ataatgttaa aattaaatca taattaggta aaaataaaat aaatataaaa gtatgagttt    3240
gttaagtttt ttataatttt ttattattaa agtaaaatta tgtatgattt ttttataatg    3300
atatgatatt ttagggatca caaaaaataa tgtggtgaat acaaaagtaa ctcaaaaaat    3360
tcatttagta aattttcatt ggagatgcta ttattatgct ttctgattgc tttgtccaaa    3420
aaataaagaa tgtttttta tttgaaaatt gaaaatttct gggtcatgtt aagatcttgt     3480
agacggtaac gtcggcctaa agttgtgtga ggggtgttgc atgcaccgat cattaattac    3540
tcgatatgga aaacgactga aataatttaa tttgatgttg ctaatattgg ccatccctct    3600
catcattatt gttttttat ttgtaacatg acatattctt gtgggtccgc tacggattgg     3660
gtgtttgttg ccaaaaaata caaaatatct gtggaacaag gataaacagt cttgtttgtt    3720
taattgattg attgatgagt ttgcaagcta tattttaat ttattttaat taaacttttg     3780
tgttttagtt ctacaatttt attcatcttg atttttttt tacttggcaa aatcatgatt     3840
ttttaatttt tacttatgtt gaaacaaat ttattgctaa aaaacatttt attctttttt     3900
tagagaaaaa acaaatttgt gatatgtagt gaatcaaatg aaaattttaa acataatata    3960
gaatactcta caaatcaatt ttgagtttct ttatcatttt atttatttat tgacatactt    4020
ctactttctg caaagaccct gactcgtgga agatataggg aaggttatgg aagttagtgt    4080
attgtcatat ctagctatct ttgctaattg aaaaagcctt ccctttgttt acagatctgg    4140
ataaggttgc atgtttattc ttttcaactg tgaatggttc tttgcatctt ttttagtata    4200
tgagattaat gttttaatta ggaagaagct tttagaacat cacccgaatc caattcgttt    4260
tggtttctgt gatcttgatg taaatctata ctaatttggt ttgggcagaa gaaaatgttc    4320
tttgctcaag tcctctagga cgaaaatata aatataacag ggtatatcag atctctattc    4380
ttctgtgggt aatgatagca tgtttctgtt gttttcttat tcttcattgg tcatgataac    4440
ctgctaattc tatttgccac gattgagatg aaaaggtaat gaactagtaa acaataatga    4500
gaagaatatg tcgctactat tgttgaaacg gttacgccag gcacttgagt atgatgcact    4560
attttaatta atgcattttt tttgctttga tgagaacgca cattgttcat tctgattcgg    4620
tgagtttaga aactattgct gataatcctt gatttaagat tttagtcttg ttcatgttca    4680
ttaaaagtgt tgtaaaaaaa tgcactgata tgtcatgtgc agattgtgtg aagatggggg    4740
cgggtggccg aactgatgtt cctcctgcca acaggaagtc agaggttgac cctttgaagc    4800
gggtgccatt tgaaaaacct ccatttagtc tcagccaaat caagaaggtc attccacctc    4860
actgtttcca gcgttctgtt ttccgctcat tctcctatgt tgtttacgac ctcaccatag    4920
ccttctgcct ctattatgtt gccacccatt acttccacct ccttcccagc cctctctctt    4980
tcttggcatg gccaatctac tgggctgtcc aaggttgcat ccttactgga gtttgggtca    5040
ttgcccatga gtgtggccac catgcattca gtgactacca gttgcttgat gatattgttg    5100
```

-continued

```
gccttgtcct ccactccggt ctcctagtcc catactttc atggaaatac agccatcgcc      5160
gtcaccactc aacactggt tctcttgagc gggatgaagt atttgtgcca aagcagaagt      5220
cctgtatcaa gtggtactct aaataccta caatcctcc aggcagagtc ctcactcttg       5280
ctgtcaccct cacacttggt tggcccttgt acttggcttt aaatgtttct ggaaggcctt    5340
atgatagatt tgcttgccac tatgacccat atggtccat ttactctgat cgtgaacgac     5400
ttcaaatata tatatcagat gcaggagtac ttgcagtatg ctatgccttt ttccgtcttg   5460
ccatggcaaa aggacttgcc tgggtggtgt gtgtttatgg agttccattg ctagtggtca    5520
atggattttt ggtgttgatt acattcttgc agcatactca ccctgcattg ccacattaca   5580
cttcctctga gtgggactgg ttgagaggag ctttagcaac agtggataga gattatggaa   5640
tcctgaacaa ggtcttccat aatattacag acactcatgt agcacatcac ttgttctcca  5700
caatgccaca ttatcatgca atggaggcta caaaggcaat aaaacccat ttgggagagt    5760
attatcggtt tgatgagact ccatttgtca aggcaatgtg gagagaggca agagagtgta  5820
tttatgtgga gccagatcaa agtaccgaga gcaaggtgt attttggtac aacaataagt    5880
tgtgatgatt aatgtagccg aggcttctt gaactttccc ttgtgactgt ttagtatcat    5940
ggttgcttat tgggaataat tttgttgaac cctgatgttg gtagtaagta tctagacagt   6000
tgcatagcgg ttttgtttac agaataagat atagcctctc tgaacagttt gattattgca   6060
ccatggtttg caatcggtgc atgtcgacca agtttctcaa gactgtggag aagcttattc   6120
ttgttccagt tcttgaatcc aagttgttac cgtattctgt aagccgaatt ctgcagatat    6180
ccatcacact ggcggccgct cgagcatgca tctagagggc                         6220
```

<210> SEQ ID NO 4
<211> LENGTH: 4597
<212> TYPE: DNA
<213> ORGANISM: Glycine max

<400> SEQUENCE: 4

```
gtacttttct ctccttatct ctttatcttt attctttcct actttattgc ttaaaccaat       60
gctatctatg cttcgatctc gccttcttat tttccacttc ccttttctcg cttgatctaa     120
ccgttttcgc cctccgcgct tcgattgact gagtacatct acgattctct gttctttcat    180
ttcatagatt tcgtctgatt ttggctaact tggtttctgt tgcggccgat tcttacatat     240
actgattgtt tagcataaat gaacttgctt gtttagcact atctgcatat tttcgtcacg    300
catctctttc ggatctaagg atgaatctcc tatttcctcc gtattattc tcgtatctct      360
tgttctgtgc taatgctcca gaaaatggca gcattgtctt cttctttgct gtataagtgt    420
ttgtgttgtg aatctggaag cgattttgcg tgaggtaact tgcgacttca actattatct    480
ttcagatctc gttaatttat tagctgctat taatttgtgt gtgcagtgtc aaactgaagc    540
acacgactgc ttagaagtta gaattgact gactgttcct ctttgatttt ttctttcctt    600
ttctttgctw actcggccta tttaatgatc tttataaata gattagtgga ccacttggtt   660
agttggtgag ttatgaatat tcgaattttc taccacaagt tgggttaaaa aaatctctgc  720
aactacacga ggattttta ttttatttag aggaaactat tctgtcatcc ttttccgat     780
tacactttc tatcagttgt tttgaaatat acacctagg aatataatat tacccctttc     840
ggtcttaata taaatatatt ttaattattt atattttatt taatgaaatt attttttaaa    900
tactttcatt taatagaatt tttaataaag ttaaagactt ttattgtgta gagtttaacg    960
aagttaatta gtttctag taatgtaaa atatgccttt tttgttgttt ataatggaga     1020
```

```
ttggaaaaaa tatactttaa ttttttttcaa gtgatgaata attatggatg ttttgtcaat      1080 attttttgtct tgctatacaa ctttcagtct tgccattaaa taattttgaa tgtgttattg      1140
atatctctga acaatattta gagacgaaca taaattttat atattttata taatttcttt      1200 ttattacccct tttattatca attttgaaat ttggttaata tctgtgtttc attttgaggt      1260
ctcaaatttg atataaggag gttcaaaatg cgttgctagc cattttaaag attagcagga      1320
gaggaaatgt ttctggactt aaatttaaaa tatgcttatt tgttttttcaa gagagagaga      1380 tcaatattta taatacac ttgaattaat atacaccatt gttgcaaaaa aaaaaaaata      1440
ttagttgatt gtgtgacaat attttatatt aaatataatt agttaattta gttcaagttg      1500
agttacattt ttacatacca ttcttagccg ccacttttt atatttattt gtaggaataa      1560
cttttcatct gtatcaattt tccccgtcta ataaaagggg tttgacttttt tcttataata      1620 gagtttttttt ttttttgctt taagttattg taaaataatt attttatttt ttttgccttt      1680
gtaaattatg tatatttaat gttttaatag gaaaaaaatg ttatcaaaag cactaaaaga      1740
ctaaaattaa acaaccataa tttgcaaaga tgaaaataaa aaaataatttt tgtaaagata      1800 aaaaatgaaa taaatagtt aaattatagg aatttaaaag ctatttaaat caacaaaagt      1860
taaagtttct gtaaaaaaag ttcaattttt tttttttatta ttgaaaaagt taaagctaat      1920
gagcgttcga tttgggttag tatgtagtat ttattatttt caagattttg gatttttattg      1980 tcgatgtttc tgatttgaat ataattattt tccattcaac ttgtgatttt ataagaaaaa      2040
aaaaggtaca gaaaaaatca agcgcttttt ttatttcaat tagtggaggt ttcactgaaa      2100
tgggtaaaga atctattttg caatcacaat tattaccggt attcaactgc aacaaggaac      2160
aaaattcctt tcgtaaatat acggagagga atctattttg acttgttgaa tttatggtaa      2220
agtagaattt agaatttaat tatgagttga agtaattttg aataatttat atgttaaata      2280
taaaattttg tactaagttt tattcataac tttgattcta taatacaaac atacataagt      2340
tcaaaaataa ttttaattaa aattaatttt atcaattttt attcaaacac gagtctaatt      2400
tgcttgatga attaagaaaa taaggaagaa aatattaaaa actaggagag aagttaaaga      2460
gaatttcatc tttattattc tcagttgttt caaaaataat gaaaggatag ctatataata      2520
ctgtaactga gccaagaaca tatttgccgt ccgagtaacc ttttcttttc ttgttccgtt      2580
ttctccgccg atgaagagag ggaagggaat gtatctttgt atttatgttt tcaaagagtt      2640
cgtgcataaa attggtttaa tcaattttt cataagatta ttatttttatg attttttaaa      2700 ataaattagt aactatattc cgtaagtcgt acacagttat atgtagtaag taaattatat      2760
tttaataatt attatcttaa aattttctta agaacttggt taaaatattt ttgtttgaaa      2820
aagtttatga taacttttttt ttgttgaaaa aaagtttacg attatctaac tcgtacttag      2880
attatttcta attgggattt attgaagggt tttttaagta aagaaattgt ttcttatggt      2940
ttctttttta ttggacaaat ttacgtagca aagagtgttt cttaaaaaca agacatgtat      3000
cctttgaaaa aaaactattt ctttgaaata aaaaataata tttatctggc acataataat      3060
gttaaaatta aatcataatt aggtaaaaat aaaataaata taaagtatg agtttgttaa      3120 gtttttttata atttttttatt attaaagtaa aattatgtat gatttttta taatgatatg      3180 atatttttagg gatcacaaaa aataatgtgg tgaatacaaa agtaactcaa aaaattcatt      3240
tagtaaattt tcattggaga tgctattatt atgctttctg attgctttgt ccaaaaaata      3300
aagaatgttt ttttatttga aaattgaaaa tttctgggtc atgttaagat cttgtagacg      3360
```

```
gtaacgtcgg cctaaagttg tgtgaggggt gttgcatgca ccgatcatta attactcgat      3420
atggaaaacg actgaaataa tttaatttga tgttgctaat attggccatc cctctcatca      3480
ttattgtttt tttatttgta acatgacata ttcttgtggg tccgctacgg attgggtgtt      3540
tgttgccaaa aaatacaaaa tatctgtgga acaaggataa acagtcttgt ttgtttaatt      3600
gattgattga tgagtttgca agctatattt taatttatt ttaattaaac ttttgtgttt       3660
tagttctaca attttattca tcttgatttt ttttttactt ggcaaaatca tgatttttta      3720
atttttactt atgttgaaaa caaatttatt gctaaaaaaa catttattct ttttttagag      3780
aaaaaacaaa tttgtgatat gtagtgaatc aaatgaaaat tttaaacata atatagaata      3840
ctctacaaat caattttgag tttctttatc attttattta tttattgaca tacttctact      3900
ttctgcaaag accctgactc gtggaagata tagggaaggt tatggaagtt agtgtattgt      3960
catatctagc tatctttgct aattgaaaaa gccttccctt tgtttacaga tctggataag      4020
gttgcatgtt tattctttt aactgtgaat ggttctttgc atcttttta gtatatgaga       4080 ttaatgtttt aattaggaag aagcttttag aacatcaccc gaatccaatt cgttttggtt      4140
tctgtgatct tgatgtaaat ctatactaat ttggtttggg cagaagaaaa tgttctttgc      4200
tcaagtcctc taggacgaaa atataaatat aacagggtat atcagatctc tattcttctg      4260
tgggtaatga tagcatgttt ctgttgtttt cttattcttc attggtcatg ataacctgct      4320
aattctattt gccacgattg agatgaaaag gtaatgaact agtaaacaat aatgagaaga      4380
atatgtcgct actattgttg aaacggttac gccaggcact tgagtatgat gcactatttt      4440
aattaatgca ttttttttgc tttgatgaga acgcacattg ttcattctga ttcggtgagt      4500
ttagaaacta ttgctgataa tccttgattt aagattttag tcttgttcat gttcattaaa      4560
agtgttgtaa aaaatgcac tgatatgtca tgtgcag                                4597

<210> SEQ ID NO 5
<211> LENGTH: 191
<212> TYPE: DNA
<213> ORGANISM: Glycine max

<400> SEQUENCE: 5
gtaataattt ttgtgtttct tactcttttt ttttttttt tgtttatgat atgaatctca        60
cacattgttc tgttatgtca tttcttcttc atttggcttt agacaactta aatttgagat       120
ctttattatg ttttttgctta tatggtaaag tgattcttca ttatttcatt cttcattgat      180
tgaattgaac a                                                            191

<210> SEQ ID NO 6
<211> LENGTH: 346
<212> TYPE: DNA
<213> ORGANISM: Glycine max

<400> SEQUENCE: 6
ttagttcata ctggcttttt tgtttgttca tttgtcattg aaaaaaaatc ttttgttgat        60
tcaattattt ttatagtgtg tttggaagcc cgtttgagaa aataagaaat cgcatctgga       120
atgtgaaagt tataactatt tagcttcatc tgtcgttgca agttctttta ttggttaaat       180
ttttatagcg tgctaggaaa cccattcgag aaaataagaa atcacatctg gaatgtgaaa       240
gttataactg ttagcttctg agtaaacgtg gaaaaccac attttggatt tggaaccaaa        300 tttttatttga taaatgacaa ccaaattgat tttgatggat tttgca                     346
```

```
<210> SEQ ID NO 7
<211> LENGTH: 142
<212> TYPE: DNA
<213> ORGANISM: Glycine max

<400> SEQUENCE: 7
gtatgtgatt aattgcttct cctatagttg ttcttgattc aattacattt tatttatttg      60
gtaggtccaa gaaaaaggg aatctttatg cttcctgagg ctgttcttga acatggctct     120
tttttatgtg tcattatctt ag                                              142

<210> SEQ ID NO 8
<211> LENGTH: 1228
<212> TYPE: DNA
<213> ORGANISM: Glycine max

<400> SEQUENCE: 8
taacaaaaat aaatagaaaa tagtgggtga acacttaaat gcgagatagt aatacctaaa     60 aaagaaaaa aatataggta taataaataa tataactttc aaaataaaaa gaaatcatag    120
agtctagcgt agtgtttgga gtgaaatgat gttcacctac cattactcaa agattttgtt    180
gtgtccctta gttcattctt attattttac atatcttact tgaaaagact ttttaattat    240
tcattgagat cttaaagtga ctgttaaatt aaaataaaaa acaagtttgt taaaacttca    300
aataaataag agtgaaggga gtgtcatttg tcttctttct tttattgcgt tattaatcac    360
gtttctcttc tcttttttttt ttttcttctc tgctttccac ccattatcaa gttcatgtga    420
agcagtggcg gatctatgta aatgagtggg gggcaattgc acccacaaga ttttatttt    480 tatttgtaca ggaataataa aataaaactt tgcccccata aaaataaat attttttctt    540 aaaataatgc aaaataaata taagaaataa aaagagaata aattattatt aattttatta    600
ttttgtactt tttatttagt ttttttagcg gttagatttt ttttcatga cattatgtaa    660 tcttttaaaa gcatgtaata ttttttatttt gtgaaataa atataaatga tcatattagt    720
ctcagaatgt ataaactaat aataatttta tcactaaaag aaattctaat ttagtccata    780
aataagtaaa acaagtgaca attatatttt atatttactt aatgtgaaat aatacttgaa    840
cattataata aaacttaatg acaggagata ttacatagtg ccataaagat attttaaaaa    900
ataaaatcat taatacactg tactactata taatattcga tatatatttt taacatgatt    960
ctcaatagaa aaattgtatt gattatattt tattagacat gaatttacaa gccccgtttt   1020
tcatttatag ctcttacctg tgatctattg ttttgcttcg ctgttttgt tggtcaaggg    1080 acttagatgt cacaatatta atactagaag taaatattta tgaaacatg taccttacct    1140 caacaaagaa agtgtggtaa gtggcaacac acgtgttgca ttttggccc agcaataaca    1200 cgtgtttttg tggtgtacta aaatggac                                       1228

<210> SEQ ID NO 9
<211> LENGTH: 625
<212> TYPE: DNA
<213> ORGANISM: Glycine max

<400> SEQUENCE: 9
gtacatttta ttgcttattc acctaaaaac aatacaatta gtacatttgt tttatctctt     60
ggaagttagt cattttcagt tgcatgattc taatgctctc tccattctta aatcatgttt    120
tcacacccac ttcatttaaa ataagaacgt gggtgttatt ttaatttcta ttcactaaca    180
tgagaaatta acttatttca agtaataatt ttaaatatt tttatgctat tattttatta    240
```

```
caaataatta tgtatattaa gtttattgat tttataataa ttatattaaa attatatcga      300 tattaattt tgattcactg atagtgtttt atattgttag tactgtgcat ttatttaaa       360 attggcataa ataatatatg taaccagctc actatactat actgggagct tggtggtgaa      420 agggttccc aaccctcctt tctaggtgta catgctttga tacttctggt accttcttat      480
atcaatataa attatatttt gctgataaaa aaacatggtt aaccattaaa ttcttttttt      540
aaaaaaaaaa ctgtatctaa actttgtatt attaaaaaga agtctgagat taacaataaa      600
ctaacactca tttggattca ctgca                                            625

<210> SEQ ID NO 10
<211> LENGTH: 98
<212> TYPE: DNA
<213> ORGANISM: Glycine max

<400> SEQUENCE: 10
ggtgagtgat ttttgactt ggaagacaac aacacattat tattataata tggttcaaaa       60
caatgacttt ttctttatga tgtgaactcc attttta                                98

<210> SEQ ID NO 11
<211> LENGTH: 115
<212> TYPE: DNA
<213> ORGANISM: Glycine max

<400> SEQUENCE: 11
ggtaactaaa ttactcctac attgttactt tttcctcctt ttttttatta tttcaattct       60
ccaattggaa atttgaaata gttaccataa ttatgtaatt gtttgatcat gtgca          115

<210> SEQ ID NO 12
<211> LENGTH: 147
<212> TYPE: DNA
<213> ORGANISM: Glycine max

<400> SEQUENCE: 12
gtaatctcac tctcacactt tctttataca tcgcacacca gtgtgggtta tttgcaacct       60
acaccgaagt aatgccctat aattaatggg gttaacacat gtccaagtcc aatattttgt     120
tcacttattt gaacttgaac atgtgta                                          147

<210> SEQ ID NO 13
<211> LENGTH: 361
<212> TYPE: DNA
<213> ORGANISM: Glycine max

<400> SEQUENCE: 13
gtatcccatt taacacaatt tgtttcatta acatttaag agaatttttt tttcaaaata        60
gttttcgaaa ttaagcaaat accaagcaaa ttgttagatc tacgcttgta cttgttttaa      120
agtcaaattc atgaccaaat tgtcctcaca agtccaaacc gtccactatt ttattttcac     180
ctactttata gcccaatttg tcatttggtt acttcagaaa agagaacccc atttgtagta     240
aatatattat ttatgaatta tggtagtttc aacataaaac atatttatgt gcagttttgc     300
catccttcaa aagaagatag aaacttactc catgttactc tgtctatatg taatttcaca     360
g                                                                      361

<210> SEQ ID NO 14
<211> LENGTH: 1037
<212> TYPE: DNA
<213> ORGANISM: Glycine max
```

```
<400> SEQUENCE: 14
gtaacaaaaa taaatagaaa atagtgagtg aacacttaaa tgttagatac taccttcttc      60
ttcttttttt tttttttttt gaggttaatg ctagataata gctagaaaga gaaagaaaga     120
caaatatagg taaaaataaa taatataacc tgggaagaag aaaacataaa aaaagaaata     180
atagagtcta cgtaatgttt ggatttttga gtgaaatggt gttcacctac cattactcaa     240
agattctgtt gtctacgtag tgtttggact ttggagtgaa atggtgttca cctaccatta     300
ctcagattct gttgtgtccc ttagttactg tcttatattc ttagggtata ttctttattt     360
tacatccttt tcacatctta cttgaaaaga ttttaattat tcattgaaat attaacgtga     420
cagttaaatt aaaataataa aaaattcgtt aaaacttcaa ataaataaga gtgaaaggat     480
catcattttt cttctttctt ttattgcgtt attaatcatg cttctcttct tttttttctt     540
cgctttccac ccatatcaaa ttcatgtgaa gtatgagaaa atcacgattc aatggaaagc     600
tacaggaacy tttttttgttt tgtttttata atcggaatta atttatactc cattttttca     660
caataaatgt tacttagtgc cttaaagata atatttgaaa aattaaaaaa attattaata     720
cactgtacta ctatataata tttgacatat atttaacatg attttctatt gaaaatttgt     780
atttattatt ttttaatcaa aacccataag gcattaattt acaagaccca tttttcattt     840
atagctttac ctgtgatcat ttatagcttt aagggactta gatgttacaa tcttaattac     900
aagtaaatat ttatgaaaaa catgtgtctt accccttaac cttacctcaa caaagaaagt     960
gtgataagtg gcaacacacg tgttgctttt ttggcccagc aataacacgt gttttttgtgg    1020
tgtacaaaaa tggacag                                                   1037

<210> SEQ ID NO 15
<211> LENGTH: 4497
<212> TYPE: DNA
<213> ORGANISM: Glycine max

<400> SEQUENCE: 15
cttgcttggt aacaacgtcg tcaagttatt attttgttct ttttttttt atcatatttc       60
ttattttgtt ccaagtatgt catattttga tccatcttga caagtagatt gtcatgtagg     120
aataggaata tcactttaaa ttttaaagca ttgattagtc tgtaggcaat attgtcttct     180
tcttcctcct tattaatatt tttattctg ccttcaatca ccagttatgg gagatggatg      240
taatactaaa taccatagtt gttctgcttg aagtttagtt gtatagttgt tctgcttgaa     300
gtttagttgt gtgtaatgtt tcagcgttgg cttcccctgt aactgctaca atggtactga     360
atatatattt tttgcattgt tcatttttttt cttttactta atcttcattg ctttgaaatt    420
aataaaacaa aaagaaggac cgaatagttt gaagtttgaa ctattgccta ttcatgtaac     480
ttattcaccc aatcttatat agttttttctg gtagagatca ttttaaattg aaggatataa    540
attaagagga aatacttgta tgtgatgtgt ggcaatttgg aagatcatgc gtagagagtt     600
taatggcagg ttttgcaaat tgacctgtag tcataattac actgggccct tcggagtttt    660
tgtgcctttt tgttgtcgct gtgtttggtt ctgcatgtta gcctcacaca gatatttagt     720
agttgttgtt ctgcatataa gcctcacacg tatactaaac gagtgaacct caaaatcatg    780
gccttacacc tattgagtga aattaatgaa cagtgcatgt gagtatgtga ctgtgacaca    840
acccccggtt tcatattgc aatgtgctac tgtggtgatt aaccttgcta cactgtcgtc      900
cttgtttgtt tccttatgta tattgatacc ataaattatt actagtatat cattttatat    960
```

-continued

```
tgtccatacc attacgtgtt tatagtctct ttatgacatg taattgaatt ttttaattat    1020
aaaaaataat aaaacttaat tacgtactat aaagagatgc tcttgactag aattgtgatc    1080
tcctagtttc ctaaccatat actaatattt gcttgtattg atagcccctc cgttcccaag    1140
agtataaaac tgcatcgaat aatacaagcc actaggcatg taaattaaa ttgtgcctgc     1200 acctcgggat atttcatgtg gggttcatca tatttgttga ggaaaagaaa ctcccgaaat    1260
tgaattatgc atttatatat ccttttttcat ttctagattt cctgaaggct taggtgtagg   1320
cacctagcta gtagctacaa tatcagcact tctctctatt gataaacaat tggctgtaat    1380
gccgcagtag aggacgatca caacatttcg tgctggttac tttttgtttt atggtcatga    1440
tttcactctc tctaatctct ccattcattt tgtagttgtc attatcttta gattttcac     1500 tacctggttt aaaattgagg gattgtagtt ctgttggtac atattacaca ttcagcaaaa    1560
caactgaaac tcaactgaac ttgtttatac tttgacacag ggtctagcaa aggaaacaac    1620
aatgggaggt agaggtcgtg tggcaaagtg gaagttcaag ggaagaagcc tctctcaagg    1680
gttccaaaca caaagccacc attcactgtt ggccaactca agaaagcaat tccaccacac    1740
tgctttcagc gctccctcct cacttcattc tcctatgttg tttatgacct ttcatttgcc    1800
ttcattttct acattgccac cacctacttc cacctccttc ctcaacccctt ttccctcatt   1860 gcatggccaa tctattgggt tctccaaggt tgccttctca ctggtgtgtg ggtgattgct    1920
cacgagtgtg gtcaccatgc cttcagcaag taccaatggg ttgatgatgt tgtgggtttg    1980
acccttcact caaacttttt agtcccttat ttctcatgga aaataagcca tcgccgccat    2040
cactccaaca caggttccct tgaccgtgat gaagtgtttg tcccaaaacc aaaatccaaa    2100
gttgcatggt tttccaagta cttaaacaac cctctaggaa gggctgtttc tcttctcgtc    2160
acactcacaa tagggtggcc tatgtattta gccttcaatg tctctggtag accctatgat    2220
agttttgcaa gccactacca cccttatgct cccatatatt ctaaccgtga gaggcttctg    2280
atctatgtct ctgatgttgc tttgttttct gtgacttact ctctctaccg tgttgcaacc    2340
ctgaaagggt tggtttggct gctatgtgtt tatggggtgc cttttgctcat tgtgaacggt    2400 tttcttgtga ctatcacata tttgcagcac acacactttg ccttgcctca ttacgattca    2460
tcagaatggg actggctgaa gggagctttg gcaactatgg acagagatta tgggattctg    2520
aacaaggtgt tcatcacat aactgatact catgtggctc accatctctt ctctacaatg     2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagctttt ctgcctaaaa tgcacgctgc acgggacaat atcattggta   3000
atttttttaa aatctgaatt gaggctactc ataatactat ccataggaca tcaaagacat    3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgattttta gattcaaatt taataattaa tctaaattaa    3300
acttaaattt tataatatat gtcttgtaat atatcaagtt ttttttttta ttattgagtt    3360
```

-continued

```
tggaaacata taataaggaa cattagttaa tattgataat ccactaagat cgacttagta    3420
ttacagtatt tggatgattt gtatgagata ttcaaacttc actcttatca taatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660
ctgattttaa taatgatgat aaataatgat taaaatattt gattctttgt taagagaaat    3720
aaggaaaaca taaatattct catggaaaaa tcagcttgta ggagtagaaa ctttctgatt    3780
ataattttaa tcaagtttaa ttcattcttt taattttatt attagtacaa aatcattctc    3840
ttgaatttag agatgtatgt tgtagcttaa tagtaatttt ttattttat aataaaattc     3900 aagcagtcaa atttcatcca ataatcgtg ttcgtgggtg taagtcagtt attccttctt     3960
atcttaatat acacgcaaag gaaaaaataa aaataaaatt cgaggaagcg cagcagcagc    4020
tgataccacg ttggttgacg aaactgataa aaagcgctgt cattgtgtct ttgtttgatc    4080
atcttcacaa tcacatctcc agaacacaaa gaagagtgac ccttcttctt gttattccac    4140
ttgcgttagg tttctacttt cttctctctc tctctctctc tcttcattcc tcattttcc    4200 ctcaaacaat caatcaattt tcattcgat tcgtaaattt ctcgattaga tcacggggtt    4260
aggtctccca ctttatcttt tcccaagcct ttctctttcc ccctttccct gtctgcccca    4320
taaaattcag gatcggaaac gaactgggtt cttgaatttc actctagatt ttgacaaatt    4380
cgaagtgtgc atgcactgat gcgacccact cccccttttt tgcattaaac aattatgaat    4440
tgaggttttt cttgcgatca tcattgcttg aattgaatca tattaggttt agattct       4497
```

<210> SEQ ID NO 16
<211> LENGTH: 18
<212> TYPE: DNA
<213> ORGANISM: Artificial sequence
<220> FEATURE:
<223> OTHER INFORMATION: PCR primer

<400> SEQUENCE: 16
atacaagcca ctaggcat                                                     18

<210> SEQ ID NO 17
<211> LENGTH: 26
<212> TYPE: DNA
<213> ORGANISM: Artificial sequence
<220> FEATURE:
<223> OTHER INFORMATION: PCR primer

<400> SEQUENCE: 17
gattggccat gcaatgaggg aaaagg                                            26

<210> SEQ ID NO 18
<211> LENGTH: 778
<212> TYPE: DNA
<213> ORGANISM: Artificial sequence
<220> FEATURE:
<221> NAME/KEY: misc_feature
<222> LOCATION: (1)..(778)
<223> OTHER INFORMATION: unsure at all n locations
<220> FEATURE:
<223> OTHER INFORMATION: PCR primer

<400> SEQUENCE: 18
atacaagcca ctaggcatgg taaattaaat tgtgcctgca cctcgggata tttcatgtgg     60

```
ggttcatcat atttgttgag gaaaagaaac tcccgaaatt gaattatgca tttatatatc      120 cttttttcatt tctagatttc ctgaaggctt aggtgtaggc acctagctag tagctacaat     180
atcagcactt ctctctattg ataaacaatt ggctgtaatg ccgcagtaga ggacgatcac      240
aacatttcgt gctggttact ttttgtttta tggtcatgat ttcactctct ctaatctctc      300
cattcatttt gtagttgtca ttatctttag attttttcact acctggttta aaattgaggg     360
attgtagttc tgttggtaca tattacacat tcagcaaaac aactgaaact caactgaact      420
tgtttatact ttgacacagg gtctagcaaa ggaaacaaca atgggaggta gaggtcgtgt      480
ggccaaagtg gaagttcaag ggaagaagcc tctctcaagg gttccaaaca caaagccacc      540
attcactgtt ggccaactca agaaagcaat tccaccacac tgctttcagc gctccctcct      600
cacttcattc tcctatgttg tttatgacct ttcatttgcc ttcatttttct acattgccac      660 cacctacttc cacctccttc ctcaacccctt tccctcatt gcatggccaa tcaagccgaa      720
ttctgcagat atccatcaca tggcggcggn tggngnaggn ntntanaggg cccaattc       778

<210> SEQ ID NO 19
<211> LENGTH: 2463
<212> TYPE: DNA
<213> ORGANISM: Glycine max

<400> SEQUENCE: 19
actatagggc acgcgtggtc gacggcccgg gctggtcctc ggtgtgactc agccccaagt      60
gacgccaacc aaacgcgtcc taactaaggt gtagaagaaa cagatagtat ataagtatac     120
catataagag gagagtgagt ggagaagcac ttctcctttt tttttctctg ttgaaattga     180
aagtgttttc cgggaaataa ataaaataaa ttaaaatctt acacactcta ggtaggtact     240
tctaatttaa tccacacttt gactctatat atgtttttaaa aataattata atgcgtactt     300
acttcctcat tatactaaat ttaacatcga tgattttatt ttctgttttct cttcttttcca    360 cctacataca tcccaaaatt tagggtgcaa ttttaagttt attaacacat gttttttagct    420 gcatgctgcc tttgtgtgtg ctcaccaaat tgcattcttc tctttatatg ttgtatttga     480
attttcacac catatgtaaa caagattacg tacgtgtcca tgatcaaata caaatgctgt     540
cttatactgg caatttgata aacagccgtc catttttttct ttttctcttt aactatatat    600
gctctagaat ctctgaagat tcctctgcca tcgaatttct ttcttggtaa caacgtcgtc     660
gttatgttat tattttattc tattttttatt ttatcatata tatttcttat tttgttcgaa    720
gtatgtcata ttttgatcgt gacaattaga ttgtcatgta ggagtaggaa tatcacttta     780
aaacattgat tagtctgtag gcaatattgt cttcttttttc ctcctttatt aatatattt     840 gtcgaagttt taccacaagg ttgattcgct ttttttgtcc ctttctcttg ttcttttttac    900 ctcaggtatt ttagtctttc atggattata agatcactga gaagtgtatg catgtaatac     960
taagcaccat agctgttctg cttgaattta tttgtgtgta aattgtaatg tttcagcgtt     1020
ggctttccct gtagctgcta caatggtact gtatatctat ttttttgcatt gttttcatttt    1080 tttcttttac ttaatcttca ttgctttgaa attaataaaa caatataata tagttttgaac    1140 tttgaactat tgcctattca tgtaattaac ttattcactg actcttattg ttttttctggt    1200 agaattcatt ttaaattgaa ggataaatta agaggcaata cttgtaaatt gacctgtcat     1260
aattacacag gacccctgttt tgtgcctttt tgtctctgtc tttggttttg catgttagcc    1320
tcacacagat atttagtagt tgttctgcat acaagcctca cacgtatact aaaccagtgg    1380
acctcaaagt catggcctta cacctattgc atgcgagtct gtgacacaac ccctggtttc     1440
```

```
catattgcaa tgtgctacgc cgtcgtcctt gtttgtttcc atatgtatat tgataccatc    1500
aaattattat atcatttata tggtctggac cattacgtgt actctttatg acatgtaatt    1560
gagtttttta attaaaaaaa tcaatgaaat ttaactacgt agcatcatat agagataatt    1620
gactagaaat ttgatgactt attctttcct aatcatattt tcttgtattg atagccccgc    1680 tgtcccttt aaactcccga gagtataaa aactgcatcg aatattacaa gatgcactct       1740
tgtcaaatga agggggggaa atgatactac aagccactag gcatggtatg atgctaaatt    1800
aaattgtgcc tgcaccccag gatatttcat gtgggattca tcatttattg aggaaaactc    1860
tccaaattga atcgtgcatt tatatttttt ttccatttct agatttcttg aaggcttatg    1920
gtataggcac ctacaattat cagcacttct ctctattgat aaacaattgg ctgtaatacc    1980
acagtagaga acgatcacaa cattttgtgc tggttacctt ttgttttatg gtcatgattt    2040
cactctctct aatctgtcac ttccctccat tcattttgta cttctcatat ttttcacttc    2100
ctggttgaaa attgtagttc tcttggtaca tactagtatt agacattcag caacaacaac    2160
tgaactgaac ttctttatac tttgacacag ggtctagcaa aggaaacaat aatgggaggt    2220
ggaggccgtg tggccaaagt tgaaattcag cagaagaagc ctctctcaag ggttccaaac    2280
acaaagccac cattcactgt tggccaactc aagaaagcca ttccaccgca ctgctttcag    2340
cgttccctcc tcacttcatt gtcctatgtt gtttatgacc tttcattggc tttcattttc    2400
tacattgcca ccacctactt ccacctcctc cctcaccct tttccctcat tgcatggcca      2460
atc                                                                    2463

<210> SEQ ID NO 20
<211> LENGTH: 44
<212> TYPE: DNA
<213> ORGANISM: Artificial sequence
<220> FEATURE:
<223> OTHER INFORMATION: PCR primer

<400> SEQUENCE: 20
cuacuacuac uactcgagac aaagcctttta gcctttagcc tatg                    44

<210> SEQ ID NO 21
<211> LENGTH: 36
<212> TYPE: DNA
<213> ORGANISM: Artificial sequence
<220> FEATURE:
<223> OTHER INFORMATION: PCR primer

<400> SEQUENCE: 21
caucaucauc auggatccca tgtctctcta tgcaag                              36

<210> SEQ ID NO 22
<211> LENGTH: 1704
<212> TYPE: DNA
<213> ORGANISM: Glycine max

<400> SEQUENCE: 22
actatagggc acgcgtggtc gacggcccgg gctggtcctc ggtgtgactc agccccaagt    60
gacgccaacc aaacgcgtcc taactaaggt gtagaagaaa cagatagtat ataagtatac    120
catataagag gagagtgagt ggagaagcac ttctcctttt ttttctctg ttgaaattga     180 aagtgttttc cgggaaataa ataaaataaa ttaaaatctt acacactcta ggtaggtact    240
tctaatttaa tccacacttt gactctatat atgttttaaa aataattata atgcgtactt    300
```

| | |
|---|---:|
| acttcctcat tatactaaat ttaacatcga tgatttttatt ttctgtttct cttcttttcca | 360 |
| cctacataca tcccaaaatt tagggtgcaa ttttaagttt attaacacat gttttttagct | 420 |
| gcatgctgcc tttgtgtgtg ctcaccaaat tgcattcttc tctttatatg ttgtatttga | 480 |
| attttcacac catatgtaaa caagattacg tacgtgtcca tgatcaaata caaatgctgt | 540 |
| cttatactgg caatttgata aacagccgtc cattttttct ttttctcttt aactatatat | 600 |
| gctctagaat ctctgaagat tcctctgcca tcgaatttct ttcttggtaa caacgtcgtc | 660 |
| gttatgttat tattttattc tattttatt ttatcatata tatttcttat tttgttcgaa | 720 |
| gtatgtcata ttttgatcgt gacaattaga ttgtcatgta ggagtaggaa tatcacttta | 780 |
| aaacattgat tagtctgtag gcaatattgt cttctttttc ctcctttatt aatatatttt | 840 |
| gtcgaagttt taccacaagg ttgattcgct ttttttgtcc ctttctcttg ttcttttttac | 900 |
| ctcaggtatt ttagtctttc atggattata agatcactga aagtgtatg catgtaatac | 960 |
| taagcaccat agctgttctg cttgaattta tttgtgtgta aattgtaatg tttcagcgtt | 1020 |
| ggctttccct gtagctgcta caatggtact gtatatctat tttttgcatt gttttcattt | 1080 |
| tttcttttac ttaatcttca ttgctttgaa attaataaaa caatataata tagttttgaac | 1140 |
| tttgaactat tgcctattca tgtaattaac ttattcactg actcttattg ttttttctggt | 1200 |
| agaattcatt ttaaattgaa ggataaatta agaggcaata cttgtaaatt gacctgtcat | 1260 |
| aattacacag gaccctgttt tgtgccttt tgtctctgtc tttggttttg catgttagcc | 1320 |
| tcacacagat atttagtagt tgttctgcat acaagcctca cacgtatact aaaccagtgg | 1380 |
| acctcaaagt catggcctta cacctattgc atgcgagtct gtgacacaac ccctggtttc | 1440 |
| catattgcaa tgtgctacgc cgtcgtcctt gtttgtttcc atatgtatat tgataccatc | 1500 |
| aaattattat atcatttata tggtctggac cattacgtgt actcttttatg acatgtaatt | 1560 |
| gagtttttta attaaaaaaa tcaatgaaat ttaactacgt agcatcatat agagataatt | 1620 |
| gactagaaat ttgatgactt attctttcct aatcatattt tcttgtattg atagccccgc | 1680 |
| tgtccctttt aaactcccga gaga | 1704 |

<210> SEQ ID NO 23
<211> LENGTH: 4010
<212> TYPE: DNA
<213> ORGANISM: Glycine max

<400> SEQUENCE: 23

| | |
|---|---:|
| acaaagcctt tagcctatgc tgccaataat ggataccaac aaaagggttc ttcttttgat | 60 |
| tttgatccta gcgctcctcc accgtttaag attgcagaaa tcagagcttc aataccaaaa | 120 |
| cattgctggg tcaagaatcc atggagatcc ctcagttatg ttctcaggga tgtgcttgta | 180 |
| attgctgcat tggtggctgc agcaattcac ttcgacaact ggcttctctg gctaatctat | 240 |
| tgccccattc aaggcacaat gttctgggct ctctttgttc ttggacatga ttggtaataa | 300 |
| tttttgtgtt tcttactctt tttttttttt ttttgtttat gatatgaatc tcacacattg | 360 |
| ttctgttatg tcatttcttc ttcatttggc tttagacaac ttaaatttga gatctttatt | 420 |
| atgttttgc ttatatggta aagtgattct tcattatttc attcttcatt gattgaattg | 480 |
| aacagtggcc atggaagctt ttcagatagc cctttgctga atagcctggt gggacacatc | 540 |
| ttgcattcct caattcttgt gccataccat ggatggtag ttcatactgg cttttttgtt | 600 |
| tgttcatttg tcattgaaaa aaaatctttt gttgattcaa ttatttttat agtgtgtttg | 660 |
| gaagcccgtt tgagaaaata agaaatcgca tctggaatgt gaaagttata actatttagc | 720 |

```
ttcatctgtc gttgcaagtt cttttattgg ttaaatttttt atagcgtgct aggaaaccca      780
ttcgagaaaa taagaaatca catctggaat gtgaaagtta taactgttag cttctgagta      840
aacgtggaaa aaccacattt tggatttgga accaaatttt atttgataaa tgacaaccaa      900
attgattttg atggattttg caggagaatt agccacagaa ctcaccatga aaccatgga       960 cacattgaga aggatgagtc atgggttcca gtatgtgatt aattgcttct cctatagttg     1020
ttcttgattc aattacattt tatttatttg gtaggtccaa gaaaaaggg aatctttatg      1080 cttcctgagg ctgttcttga acatggctct tttttatgtg tcattatctt agttaacaga    1140
gaagatttac aagaatctag acagcatgac aagactcatt agattcactg tgccatttcc    1200
atgtttgtgt atccaattta tttggtgagt gattttttga cttggaagac aacaacacat    1260
tattattata atatggttca aaacaatgac ttttttcttta tgatgtgaac tccatttttt    1320
agttttcaag aagccccgga aaggaaggct ctcacttcaa tccctacagc aatctgtttc    1380
cacccagtga gagaaaagga atagcaatat caacactgtg ttgggctacc atgttttctc    1440
tgcttatcta tctctcattc attaactagt ccacttctag tgctcaagct ctatggaatt    1500
ccatattggg taactaaatt actcctacat tgttactttt tcctcctttt ttttattatt    1560
tcaattctcc aattgaaat ttgaaatagt taccataatt atgtaattgt ttgatcatgt     1620
gcagatgttt gttatgtggc tggactttgt cacatacttg catcaccatg gtcaccacca    1680
gaaactgcct tggtaccgcg gcaaggtaac aaaaataaat agaaatagt gggtgaacac     1740 ttaaatgcga gatagtaata cctaaaaaaa gaaaaaaata taggtataat aaataatata    1800
actttcaaaa taaaaagaaa tcatagagtc tagcgtagtg tttggagtga aatgatgttc    1860
acctaccatt actcaaagat tttgttgtgt cccttagttc attcttatta ttttacatat    1920
cttacttgaa aagactttt aattattcat tgagatctta aagtgactgt taaattaaaa     1980
taaaaaacaa gtttgttaaa acttcaaata aataagagtg aagggagtgt catttgtctt    2040 cttttctttta ttgcgttatt aatcacgttt ctcttctctt ttttttttt cttctctgct   2100 ttccacccat tatcaagttc atgtgaagca gtggcggatc tatgtaaatg agtgggggc     2160 aattgcaccc acaagatttt atttttttatt tgtacaggaa taataaaata aactttgcc    2220 cccataaaaa ataaatattt tttcttaaaa taatgcaaaa taaatataag aaataaaaag    2280
agaataaatt attattaatt ttattatttt gtactttta tttagttttt ttagcggtta     2340
gatttttttt tcatgacatt atgtaatctt ttaaaagcat gtaatatttt tatttgtga    2400 aaataaatat aaatgatcat attagtctca gaatgtataa actaataata attttatcac    2460
taaaagaaat tctaatttag tccataaata agtaaaacaa gtgacaatta tattttatat    2520
ttacttaatg tgaaataata cttgaacatt ataataaaac ttaatgacag gagatattac    2580
atagtgccat aaagatattt taaaaaataa aatcattaat acactgtact actatataat    2640
attcgatata tattttttaac atgattctca atagaaaaat tgtattgatt atattttatt    2700
agacatgaat ttacaagccc cgttttttcat ttatagctct tacctgtgat ctattgtttt    2760
gcttcgctgt ttttgttggt caagggactt agatgtcaca atattaatac tagaagtaaa    2820
tatttatgaa aacatgtacc ttacctcaac aaagaaagtg tggtaagtgg caacacacgt    2880
gttgcatttt tggcccagca ataacacgtg ttttttgtggt gtactaaaat ggacaggaat    2940
ggagttattt aagaggtggc ctcaccactg tggatcgtga ctatggttgg atcaataaca    3000
ttcaccatga cattggcacc catgttatcc accatctttt cccccaaatt cctcattatc     3060
```

```
acctcgttga agcggtacat tttattgctt attcacctaa aaacaataca attagtacat    3120
ttgttttatc tcttggaagt tagtcatttt cagttgcatg attctaatgc tctctccatt    3180
cttaaatcat gttttcacac ccacttcatt taaaataaga acgtgggtgt tatttttaatt   3240 tctattcact aacatgagaa attaacttat ttcaagtaat aattttaaaa tattttttatg   3300 ctattatttt attacaaata attatgtata ttaagtttat tgattttata ataattatat    3360
taaaattata tcgatattaa ttttgattc actgatagtg ttttatattg ttagtactgt     3420
gcatttattt taaaattggc ataaataata tatgtaacca gctcactata ctatactggg    3480
agcttggtgg tgaaaggggt tcccaaccct cctttctagg tgtacatgct ttgatacttc    3540
tggtaccttc ttatatcaat ataaattata ttttgctgat aaaaaaacat ggttaaccat    3600
taaattcttt ttttaaaaaa aaaactgtat ctaaactttg tattattaaa aagaagtctg    3660
agattaacaa taaactaaca ctcatttgga ttcactgcag acacaagcag caaaaccagt    3720
tcttggagat tactaccgtg agccagaaag atctgcgcca ttaccatttc atctaataaa    3780
gtatttaatt cagagtatga gacaagacca cttcgtaagt gacactggag atgttgttta    3840
ttatcagact gattctctgc tcctccactc gcaacgagac tgagtttcaa acttttgggg    3900
ttattattta ttgattctag ctactcaaat tacttttttt ttaatgttat gttttttgga    3960
gtttaacgtt ttctgaacaa cttgcaaatt acttgcatag agagacatgg               4010

<210> SEQ ID NO 24
<211> LENGTH: 34
<212> TYPE: DNA
<213> ORGANISM: Artificial sequence
<220> FEATURE:
<223> OTHER INFORMATION: PCR primer

<400> SEQUENCE: 24
acgaattcct cgaggtaaat taaattgtgc ctgc                                34

<210> SEQ ID NO 25
<211> LENGTH: 33
<212> TYPE: DNA
<213> ORGANISM: Artificial sequence
<220> FEATURE:
<223> OTHER INFORMATION: PCR primer

<400> SEQUENCE: 25
gcgagatcta tcgatctgtg tcaaagtata aac                                 33

<210> SEQ ID NO 26
<211> LENGTH: 19
<212> TYPE: DNA
<213> ORGANISM: Artificial sequence
<220> FEATURE:
<223> OTHER INFORMATION: PCR primer

<400> SEQUENCE: 26
catgctttct gtgcttctc                                                 19

<210> SEQ ID NO 27
<211> LENGTH: 19
<212> TYPE: DNA
<213> ORGANISM: Artificial sequence
<220> FEATURE:
<223> OTHER INFORMATION: PCR primer

<400> SEQUENCE: 27
gttgatccaa ccatagtcg                                                 19
```

<210> SEQ ID NO 28
<211> LENGTH: 36
<212> TYPE: DNA
<213> ORGANISM: Artificial sequence
<220> FEATURE:
<223> OTHER INFORMATION: PCR primer

<400> SEQUENCE: 28
gcgatcgatg tatgatgcta aattaaattg tgcctg                          36

<210> SEQ ID NO 29
<211> LENGTH: 30
<212> TYPE: DNA
<213> ORGANISM: Artificial sequence
<220> FEATURE:
<223> OTHER INFORMATION: PCR primer

<400> SEQUENCE: 29
gcggaattcc tgtgtcaaag tataaagaag                                 30

<210> SEQ ID NO 30
<211> LENGTH: 30
<212> TYPE: DNA
<213> ORGANISM: Artificial sequence
<220> FEATURE:
<223> OTHER INFORMATION: PCR primer

<400> SEQUENCE: 30
gatcgatgcc cggggtaata atttttgtgt                                 30

<210> SEQ ID NO 31
<211> LENGTH: 29
<212> TYPE: DNA
<213> ORGANISM: Artificial sequence
<220> FEATURE:
<223> OTHER INFORMATION: PCR primer

<400> SEQUENCE: 31
cacgcctcga gtgttcaatt caatcaatg                                  29

<210> SEQ ID NO 32
<211> LENGTH: 24
<212> TYPE: DNA
<213> ORGANISM: Artificial sequence
<220> FEATURE:
<223> OTHER INFORMATION: PCR primer

<400> SEQUENCE: 32
cactcgagtt agttcatact ggct                                       24

<210> SEQ ID NO 33
<211> LENGTH: 25
<212> TYPE: DNA
<213> ORGANISM: Artificial sequence
<220> FEATURE:
<223> OTHER INFORMATION: PCR primer

<400> SEQUENCE: 33
cgcatcgatt gcaaaatcca tcaaa                                      25

<210> SEQ ID NO 34
<211> LENGTH: 38
<212> TYPE: DNA
<213> ORGANISM: Artificial sequence
<220> FEATURE:

-continued

```
<223> OTHER INFORMATION: PCR primer

<400> SEQUENCE: 34
cuacuacuac uactcgagcg taaatagtgg gtgaacac                        38

<210> SEQ ID NO 35
<211> LENGTH: 41
<212> TYPE: DNA
<213> ORGANISM: Artificial sequence
<220> FEATURE:
<223> OTHER INFORMATION: PCR primer

<400> SEQUENCE: 35
caucaucauc auctcgagga attcgtccat tttagtacac c                   41

<210> SEQ ID NO 36
<211> LENGTH: 39
<212> TYPE: DNA
<213> ORGANISM: Artificial sequence
<220> FEATURE:
<223> OTHER INFORMATION: PCR primer

<400> SEQUENCE: 36
cuacuacuac uactcgaggc gcgtacattt tattgctta                       39

<210> SEQ ID NO 37
<211> LENGTH: 41
<212> TYPE: DNA
<213> ORGANISM: Artificial sequence
<220> FEATURE:
<223> OTHER INFORMATION: PCR primer

<400> SEQUENCE: 37
caucaucauc auctcgagga attctgcagt gaatccaaat g                   41

<210> SEQ ID NO 38
<211> LENGTH: 22
<212> TYPE: DNA
<213> ORGANISM: Artificial sequence
<220> FEATURE:
<223> OTHER INFORMATION: PCR primer

<400> SEQUENCE: 38
caccatggtc atcatcagaa ac                                         22

<210> SEQ ID NO 39
<211> LENGTH: 22
<212> TYPE: DNA
<213> ORGANISM: Artificial sequence
<220> FEATURE:
<223> OTHER INFORMATION: PCR primer

<400> SEQUENCE: 39
tcacgatcca cagttgtgag ac                                         22
```

US 7,067,722 B2

NUCLEIC ACID SEQUENCES AND METHODS OF USE FOR THE PRODUCTION OF PLANTS WITH MODIFIED POLYUNSATURATED FATTY ACIDS

CROSS-REFERENCE TO RELATED APPLICATIONS

This application is a continuation-in-part of, and claims the benefit under 35 U.S.C. §120 of U.S. patent application Ser. No. 09/638,508, filed Aug. 11, 2000, now abandoned, which application claims priority to U.S. Provisional Application Ser. No. 60/151,224, filed Aug. 26, 1999 and U.S. Provisional Application Ser. No. 60/172,128, filed Dec. 17, 1999, all of which applications are herein incorporated by reference in their entireties.

INCORPORATION OF SEQUENCE LISTING

A paper copy of the Sequence Listing and a computer readable form of the sequence listing on diskette, containing the file named Seq List 16518-056.txt, which is 43,401 bytes in size (measured in MS-DOS), and which was created on Mar. 20, 2002, are herein incorporated by reference.

FIELD OF THE INVENTION

The present invention is directed to nucleic acid molecules and nucleic acid constructs, and other agents associated with fatty acid synthesis. Moreover, the present invention is directed to plants incorporating such agents where the plants exhibit altered ratios of saturated and unsaturated fats. In particular, the present invention is directed to plants incorporating such agents where the plants exhibit altered ratios of monounsaturated to polyunsaturated fatty acids.

BACKGROUND

Plant oils are used in a variety of applications. Novel vegetable oils compositions and improved means to obtain oils compositions, from biosynthetic or natural plant sources, are needed. Depending upon the intended oil use, various different fatty acid compositions are desired.

Higher plants appear to synthesize fatty acids via a common metabolic pathway—the fatty acid synthetase (FAS) pathway. In developing seeds, where fatty acids are attached to glycerol backbones, forming triglycerides, for storage as a source of energy for further germination, the FAS pathway is located in the plastids. The first committed step is the formation of acetyl-ACP (acyl carrier protein) from acetyl-CoA and ACP catalyzed by the enzyme, acetyl-CoA:ACP transacylase (ATA). Elongation of acetyl-ACP to 16- and 18-carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-ketoacyl-ACP dehydratase), and finally reduction of the enoyl-ACP to form the elongated saturated acyl-ACP (enoyl-ACP reductase). β-ketoacyl-ACP synthase I catalyzes elongation up to palmitoyl-ACP (C16:0), whereas β-ketoacyl-ACP synthase II catalyzes the final elongation to stearoyl-ACP (C18:0). Common plant unsaturated fatty acids, such as oleic, linoleic and linolenic acids found in storage triglycerides, originate from the desaturation of stearoyl-ACP to form oleoyl-ACP (C 18:1) in a reaction catalyzed by a soluble plastid Δ-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound Δ-12 desaturase and Δ-15 desaturase. These "desaturases" thus create polyunsaturated fatty acids.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of an enzyme source with useful kinetic properties, purification of the protein of interest to a level which will allow for its amino acid sequencing, utilizing amino acid sequence data to obtain a nucleic acid sequence capable to use as a probe to retrieve the desired DNA sequence, and the preparation of constructs, transformation and analysis of the resulting plants.

Thus, additional nucleic acid targets and methods for modifying fatty acid compositions are needed. In particular, constructs and methods to produce a variety of ranges of different fatty acid compositions are needed.

SUMMARY OF THE INVENTION

The present invention provides a substantially purified nucleic acid molecule comprising a nucleic acid sequence with at least 70% sequence identity to SEQ ID NO:12 or its complement. Also provided by the present invention is a substantially purified nucleic acid molecule comprising a nucleic acid sequence with at least 70% sequence identity to SEQ ID NO:13 or its complement.

The present invention provides a substantially purified nucleic acid molecule comprising a nucleic acid sequence with at least 70% sequence identity to SEQ ID NO:14 or its complement. The present invention also provides a substantially purified nucleic acid molecule comprising a nucleic acid sequence with at least 70% sequence identity to SEQ ID NO:4 or its complement.

Further provided by the present invention are a nucleic acid molecule comprising at least 15 consecutive nucleotides of a nucleic acid molecule having the sequence of SEQ ID NO:12; a nucleic acid molecule comprising at least 15 consecutive nucleotides of a nucleic acid molecule having the sequence of SEQ ID NO:13; a nucleic acid molecule comprising at least 15 consecutive nucleotides of a nucleic acid molecule having the sequence of SEQ ID NO:14; and a nucleic acid molecule comprising at least 15 consecutive nucleotides of a nucleic acid molecule having the sequence of SEQ ID NO:4.

Also provided by the present invention is a recombinant nucleic acid molecule comprising as operably linked components: (A) a promoter that functions in a plant cell to cause production of an mRNA molecule; and (B) a nucleic acid sequence that hybridizes under high stringency conditions to a nucleic acid sequence selected from the group consisting of SEQ ID NO:12 and complements thereof.

Also provided by the present invention is a recombinant nucleic acid molecule comprising as operably linked components: (A) a promoter that functions in a plant cell to cause production of an mRNA molecule; and (B) a nucleic acid sequence that hybridizes under high stringency conditions to a nucleic acid sequence selected from the group consisting of SEQ ID NO:13 and complements thereof.

The present invention also provides a recombinant nucleic acid molecule comprising as operably linked components:

(A) a promoter that functions in a plant cell to cause production of an mRNA molecule; and (B) a nucleic acid sequence that hybridizes under high stringency conditions to a nucleic acid sequence selected from the group consisting of SEQ ID NO:14 and complements thereof.

Also provided by the present invention is a recombinant nucleic acid molecule comprising as operably linked components: (A) a promoter that functions in a plant cell to cause production of an mRNA molecule; and (B) a nucleic acid sequence that hybridizes under high stringency conditions to a nucleic acid sequence selected from the group consisting of SEQ ID NO:4 and complements thereof.

Further provided by the present invention is a transformed soybean plant having a nucleic acid molecule that comprises (a) a first promoter operably linked to a first nucleic acid molecule having a first nucleic acid sequence that has 85% or greater identity to a nucleic acid sequence selected from the group consisting of SEQ ID NO:1, 2 and complements and fragments thereof, and (b) a second nucleic acid molecule having a second nucleic acid sequence that has 85% or greater identity to a nucleic acid sequence selected from the group consisting of SEQ ID NO:4 through SEQ ID NO:14 and complements and fragments thereof, wherein the second nucleic acid molecule is operably linked to the first promoter or a second promoter.

The present invention also provides a method of producing a soybean plant having a seed with reduced linolenic acid content comprising: transforming a soybean plant with a nucleic acid molecule that comprises (a) a first promoter operably linked to a first nucleic acid molecule having a first nucleic acid sequence that has 85% or greater identity to a nucleic acid sequence selected from the group consisting of SEQ ID NO:1, 2 and complements thereof, and (b) a second nucleic acid molecule having a second nucleic acid sequence that has 85% or greater identity to a nucleic acid sequence selected from the group consisting of SEQ ID NO:4 through SEQ ID NO:14 and complements thereof, wherein the second nucleic acid molecule is operably linked to the first promoter or a second promoter; and growing said plant, wherein said plant produces seed with less linolenic acid than a plant having a similar genetic background but lacking said nucleic acid molecule.

The present invention also provides a method of producing a soybean plant having a seed with increased oleic acid content comprising: transforming a soybean plant with a nucleic acid molecule that comprises (a) a promoter operably linked to a first nucleic acid molecule having a first nucleic acid sequence that has 85% or greater identity to a nucleic acid sequence selected from the group consisting of SEQ ID NO:1, 2 and complements thereof, and (b) a second nucleic acid molecule having a second nucleic acid sequence that has 85% or greater identity to a nucleic acid sequence selected from the group consisting of SEQ ID NO:4 through SEQ ID NO:14 and complements thereof, wherein the second nucleic acid molecule is operably linked to the first promoter or a second promoter; and growing said plant, wherein said plant produces seed with more oleic acid than a plant having a similar genetic background but lacking said nucleic acid molecule.

Also provided by the present invention is a transformed soybean plant having two or more nucleic acid molecules wherein each nucleic acid molecule is operably linked to a promoter and wherein each nucleic acid molecule has a nucleic acid sequence that has 85% or greater identity to a nucleic acid sequence selected from the group consisting of SEQ ID NOs:1, 2, and 4–14 and complements and fragments thereof.

The present invention provides a transformed soybean plant, wherein the level of a transcript encoded by a gene selected from the group consisting of FAD2-1A, FAD2-1B, FAD2-2B, FAD3-1A, FAD3-1B, FAD3-1C is selectively reduced while leaving the level of a transcript encoded by a different gene selected from the group consisting of FAD2-1A, FAD2-1B, FAD2-2B, FAD3-1A, FAD3-1B, FAD3-1C at least partially unaffected.

The present invention also provides a method of producing a plant having a seed with a modified oil composition comprising: transforming a plant with a nucleic acid molecule that comprises, as operably linked components, a first promoter and a first nucleic acid molecule having a first nucleic acid sequence that has 85% or greater identity to a nucleic acid sequence selected from the group consisting of SEQ ID NO:1, 2, 4 through 14 and complements thereof; and, growing said plant, wherein said plant produces seed with a modified oil composition compared to a plant having a similar genetic background but lacking said nucleic acid molecule.

The present invention further provides a method of producing a plant having a seed with an altered ratio of monounsaturated to polyunsaturated fatty acids comprising: transforming a plant with a construct that comprises, as operably linked components, two or more nucleic acid molecules, each having a nucleic acid sequence that has 85% or greater identity to a nucleic acid sequence selected from the group consisting of SEQ ID NO:1, 2, 4 through 14 and complements thereof, wherein each nucleic acid molecule is operably linked to a promoter; and, growing said plant, wherein said plant produces seed with an altered ratio of monounsaturated to polyunsaturated fatty acids compared to a plant having a similar genetic background but lacking said two or more nucleic acid molecules.

DETAILED DESCRIPTION OF THE INVENTION

Description of the Nucleic Acid Sequences

SEQ ID NO:1 sets forth a nucleic acid sequence of a FAD2-1A intron 1.

SEQ ID NO:2 sets forth a nucleic acid sequence of a FAD2-1B intron 1.

SEQ ID NO:3 sets forth a nucleic acid sequence of a partial FAD2-2 genomic clone.

SEQ ID NO:4 sets forth a nucleic acid sequence of a FAD2-2B intron 1.

SEQ ID NO:5 sets forth a nucleic acid sequence of a FAD3-1A intron 1.

SEQ ID NO:6 sets forth a nucleic acid sequence of a FAD3-1A intron 2.

SEQ ID NO:7 sets forth a nucleic acid sequence of a FAD3-1A intron 3A.

SEQ ID NO:8 sets forth a nucleic acid sequence of a FAD3-1A intron 4

SEQ ID NO:9 sets forth a nucleic acid sequence of a FAD3-1A intron 5.

SEQ ID NO:10 sets forth a nucleic acid sequence of a FAD3-1A intron 3B.

SEQ ID NO:11 sets forth a nucleic acid sequence of a FAD3-1A intron 3C.

SEQ ID NO:12 sets forth a nucleic acid sequence of a FAD3-1B intron 3C.

SEQ ID NO:13 sets forth a nucleic acid sequence of a FAD3-1B intron 4.

SEQ ID NO:14 sets forth a nucleic acid sequence of a FAD3-1C intron 4.

SEQ ID NO:15 sets forth a cDNA sequence of a FAD2-1A gene sequence.

SEQ ID NOs:16 and 17 set forth nucleic acid sequences of FAD2-1A PCR primers.

SEQ ID NO:18 sets forth a nucleic acid sequence of a partial FAD2-1A genomic clone.

SEQ ID NO:19 sets forth a nucleic acid sequence of a partial FAD2-1B genomic clone.

SEQ ID NOs:20 and 21 set forth nucleic acid sequences of FAD3-1A PCR primers.

SEQ ID NO:22 sets forth a nucleic acid sequence of a FAD2-1B promoter.

SEQ ID NO:23 sets forth a nucleic acid sequence of a partial FAD3-1A genomic clone.

SEQ ID NOs:24 through 39 set forth nucleic acid sequences of PCR primers.

Definitions

As used herein, the term "gene" is used to refer to the nucleic acid sequence that encompasses the 5' promoter region associated with the expression of the gene product, any intron and exon regions and 3' untranslated regions associated with the expression of the gene product.

As used herein, a "FAD2", "Δ12 desaturase" or "omega-6 desaturase" gene is a gene that encodes an enzyme capable of catalyzing the insertion of a double bond into a fatty acyl moiety at the twelfth position counted from the carboxyl terminus.

When referring to proteins and nucleic acids herein, the use of plain capitals, e.g., "FAD2", indicates a reference to an enzyme, protein, polypeptide, or peptide, and the use of italicized capitals, e.g., "FAD2", indicates a reference to nucleic acids, including without limitation genes, cDNAs, and mRNAs.

As used herein the terminology "FAD2-1" is used to refer to a FAD2 gene that is naturally expressed in a specific manner in seed tissue.

As used herein the terminology "FAD2-2" is used to refer a FAD2 gene that is (a) a different gene from a FAD2-1 gene and (b) is naturally expressed in multiple tissues, including the seed.

As used herein, a "FAD3", "Δ15 desaturase" or "omega-3 desaturase" gene is a gene that encodes an enzyme capable of catalyzing the insertion of a double bond into a fatty acyl moiety at the fifteenth position counted from the carboxyl terminus.

As used herein the terminology "FAD3-1" is used to refer a FAD3 gene that is naturally expressed in multiple tissues, including the seed.

As used herein the capital letter that follows the gene-terminology (A, B, C) is used to designate the family member, i.e. FAD2-1A is a different gene family member from FAD2-1B.

As used herein, a "mid-oleic soybean seed" is a seed having between 50% and 75% oleic acid present in the oil composition of the seed.

As used herein, a "high oleic soybean seed" is a seed with oil having greater than 75% oleic acid present in the oil composition of the seed.

The term "non-coding" refers to sequences of nucleic acid molecules that do not encode part or all of an expressed protein. Non-coding sequences include but are not limited to introns, promoter regions, 3' untranslated regions, and 5' untranslated regions.

The term "intron" as used herein refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein.

The term "exon" as used herein refers to the normal sense of the term as meaning a segment of nucleic acid molecules, usually DNA, that encodes part of or all of an expressed protein.

As used herein, a promoter that is "operably linked" to one or more nucleic acid sequences is capable of driving expression of one or more nucleic acid sequences, including multiple coding or non-coding nucleic acid sequences arranged in a polycistronic configuration.

As used herein, the term complement of a nucleic acid sequence refers to the complement of the sequence along its complete length.

As used herein, any range set forth is inclusive of the end points of the range unless otherwise stated.

Agents

The agents of the invention will preferably be "biologically active" with respect to either a structural attribute, such as the capacity of a nucleic acid molecule to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, greater than 75% free, preferably greater than 90% free, and most preferably greater than 95% free from the other molecules (exclusive of solvent) present in the natural mixture. The term "substantially purified" is not intended to encompass molecules present in their native environmental conditions.

The agents of the invention may also be recombinant. As used herein, the term "recombinant" means any agent (e.g., including but limited to DNA, peptide), that is, or results, however indirectly, from human manipulation of a nucleic acid molecule.

It is understood that the agents of the invention may be labeled with reagents that facilitate detection of the agent (e.g., fluorescent labels, Prober et al., Science 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Nucleic Acid Molecules

Agents of the invention include nucleic acid molecules. In an aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene partially unaffected. In a preferred aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene substantially unaffected. In a highly preferred aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene essentially unaffected.

In a preferred aspect, the capability of a nucleic acid molecule to selectively reduce the level of a gene relative to another gene is carried out by a comparison of levels of mRNA transcripts. In another preferred aspect of the present invention, the nucleic acid molecule of the invention comprises a nucleic acid sequence selected from the group consisting of SEQ ID NOs:1 through 15, 18, 19, 22, 23 and complements thereof and fragments of either. In another preferred aspect of the present invention the nucleic acid molecule of the invention comprises a nucleic acid sequence selected from the group consisting of SEQ ID NOs:16, 17, 20, 21, 24 through 39, and complements thereof.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis. The cell or organism can be, or can be derived from, a plant, plant cell, algae cell, algae, fungal cell, fungus, or bacterial cell.

As used herein, "essentially unaffected" refers to a level of an agent such as a protein or mRNA transcript that is either not altered by a particular event or altered only to an extent that does not affect the physiological function of that agent. In a preferred aspect, the level of the agent that is essentially unaffected is within 20%, more preferably within 10%, and even more preferably within 5% of the level at which it is found in a cell or organism that lacks a nucleic acid molecule capable of selectively reducing another agent.

As used herein, "substantially unaffected" refers to a level of an agent such as a protein or mRNA transcript in which the level of the agent that is substantially unaffected is within 49%, more preferably within 35%, and even more preferably within 24% of the level at which it is found in a cell or organism that lacks a nucleic acid molecule capable of selectively reducing another agent.

As used herein, "partially unaffected" refers to a level of an agent such as a protein or mRNA transcript in which the level of the agent that is partially unaffected is within 80%, more preferably within 65%, and even more preferably within 50% of the level at which it is found in a cell or organism that lacks a nucleic acid molecule capable of selectively reducing another agent.

As used herein, "a selective reduction" of an agent such as a protein or mRNA is relative to a cell or organism lacking a nucleic acid molecule capable of selectively reducing the agent. In a preferred aspect, the level of the agent is selectively reduced by at least 50%, preferably at least more than 75%, and even more preferably by at least more than 90% or 95%.

When levels of an agent are compared, such a comparison is preferably carried out between organisms with a similar genetic background. In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

In an embodiment of the present invention, a nucleic acid molecule, when introduced into a cell or organism, is capable of selectively reducing the level of a protein and/or transcript encoded by a FAD2 gene while leaving the level of a protein and/or transcript encoded by a second FAD2 gene partially unaffected, substantially unaffected, or essentially unaffected. In a preferred aspect, the capability of a nucleic acid molecule to selectively reduce the level of a gene relative to another gene is carried out by a comparison of levels of mRNA transcripts. As used herein, mRNA transcripts include processed and non-processed mRNA transcripts.

In another embodiment, a nucleic acid molecule, when introduced into a cell or organism, is capable of selectively reducing the level of a protein and/or transcript encoded by a FAD2-1 gene while leaving the level of a protein and/or transcript encoded by a FAD2-2 gene partially unaffected, substantially unaffected, or essentially unaffected. In a different embodiment, a nucleic acid molecule, when introduced into a cell or organism, is capable of selectively reducing the level of a protein and/or transcript encoded by a FAD2-2 gene while leaving the level of a protein and/or transcript encoded by a FAD2-1 gene partially unaffected, substantially unaffected, or essentially unaffected.

In a further embodiment, a nucleic acid molecule, when introduced into a cell or organism, is capable of selectively reducing the level of a protein and/or transcript encoded by a FAD2 gene while leaving the level of a protein and/or transcript encoded by a FAD3 gene partially unaffected, substantially unaffected, or essentially unaffected. In a preferred embodiment, a nucleic acid molecule, when introduced into a cell or organism, is capable of selectively reducing the level of a protein and/or transcript encoded by a FAD2-1 gene while leaving the level of a protein and/or transcript encoded by a FAD3 gene partially unaffected, substantially unaffected, or essentially unaffected.

In a different embodiment, a nucleic acid molecule, when introduced into a cell or organism, is capable of selectively reducing the level of a protein and/or transcript encoded by a FAD3 gene while leaving the level of a protein and/or transcript encoded by another FAD3 gene partially unaffected, substantially unaffected, or essentially unaffected.

In an additional embodiment, a nucleic acid molecule, when introduced into a cell or organism, is capable of selectively reducing the level of a protein and/or transcript encoded by a FAD3-1C gene while leaving the level of a protein and/or transcript encoded by a FAD3-1B gene partially unaffected, substantially unaffected, or essentially unaffected. In an additional embodiment, a nucleic acid molecule, when introduced into a cell or organism, is capable of selectively reducing the level of a protein and/or transcript encoded by a FAD3-1C gene while leaving the level of a protein and/or transcript encoded by a FAD3-1A gene partially unaffected, substantially unaffected, or essentially unaffected.

In a different embodiment, a nucleic acid molecule, when introduced into a cell or organism, is capable of selectively reducing the level of a protein and/or transcript encoded by a FAD3-1B gene while leaving the level of a protein and/or transcript encoded by a FAD3-1C gene partially unaffected, substantially unaffected, or essentially unaffected. In a different embodiment, a nucleic acid molecule, when introduced into a cell or organism, is capable of selectively reducing the level of a protein and/or transcript encoded by a FAD3-1B gene while leaving the level of a protein and/or transcript encoded by a FAD3-1A gene partially unaffected, substantially unaffected, or essentially unaffected.

In a further embodiment, a nucleic acid molecule, when introduced into a cell or organism, is capable of selectively reducing the level of a protein and/or transcript encoded by a FAD3-1A gene while leaving the level of a protein and/or transcript encoded by a FAD3-1B gene partially unaffected, substantially unaffected, or essentially unaffected. In an additional embodiment, a nucleic acid molecule, when introduced into a cell or organism, is capable of selectively reducing the level of a protein and/or transcript encoded by a FAD3-1A gene while leaving the level of a protein and/or transcript encoded by a FAD3-1C gene partially unaffected, substantially unaffected, or essentially unaffected.

Further preferred embodiments of the invention are nucleic acid molecules that are at least 50%, 60%, or 70% identical over their entire length to a nucleic acid molecule of the invention, and nucleic acid molecules that are complementary to such nucleic acid molecules. More preferable are nucleic acid molecules that comprise a region that is at least 80% or 85% identical over its entire length to a nucleic acid molecule of the invention and nucleic acid molecules that are complementary thereto. In this regard, nucleic acid molecules at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

The invention also provides a nucleic acid molecule comprising a nucleic acid molecule sequence obtainable by screening an appropriate library containing the complete gene for a nucleic acid molecule sequence set forth in the Sequence Listing under stringent hybridization conditions with a probe having the sequence of said nucleic acid molecule sequence or a fragment thereof; and isolating said nucleic acid molecule sequence. Fragments useful for obtaining such a nucleic acid molecule include, for example, probes and primers as described herein.

Nucleic acid molecules of the invention can be used as a hybridization probe for RNA, cDNA, or genomic DNA to isolate full length cDNAs or genomic clones and to isolate cDNA or genomic clones of other genes that have a high sequence similarity to a nucleic acid molecule set forth in the Sequence Listing.

The nucleic acid molecules of the present invention can be readily obtained by using the herein described nucleic acid molecules or fragments thereof to screen cDNA or genomic libraries obtained from plant species or other appropriate organisms. These methods are known to those of skill in the art, as are methods for forming such libraries. In one embodiment, such sequences are obtained by incubating nucleic acid molecules of the present invention with members of genomic libraries and recovering clones that hybridize to such nucleic acid molecules thereof. In a second embodiment, methods of chromosome walking or inverse PCR may be used to obtain such sequences. In a third embodiment, the sequence of a nucleic acid molecule of the present invention may be used to screen a library or database, using bioinformatics techniques known in the art. See, e.g., *Bioinformatics*, Baxevanis & Ouellette, eds., Wiley-Interscience (1998).

Any of a variety of methods may be used to obtain one or more of the nucleic acid molecules of the present invention. Automated nucleic acid synthesizers may be employed for this purpose, and to make a nucleic acid molecule that has a sequence also found in a cell or organism. In lieu of such synthesis, the disclosed nucleic acid molecules may be used to define a pair of primers that can be used with the polymerase chain reaction to amplify and obtain any desired nucleic acid molecule or fragment.

"Identity," as is well understood in the art, is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J. Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12:76–80 (1994); Birren et al., *Genome Analysis*, 1:543–559 (1997)). The BLASTX program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well-known Smith Waterman algorithm can also be used to determine identity.

Parameters for polypeptide sequence comparison typically include the following:

Algorithm: Needleman and Wunsch, *J. Mol. Biol.*, 48:443–453 (1970)

Comparison matrix: BLOSSUM62 from Hentikoff and Hentikoff, *Proc. Natl. Acad. Sci. USA*, 89:10915–10919 (1992)

Gap Penalty: 12

Gap Length Penalty: 4

A program which can be used with these parameters is publicly available as the "gap" program from Genetics Computer Group, Madison, Wis. The above parameters along with no penalty for end gap are the default parameters for peptide comparisons.

Parameters for nucleic acid molecule sequence comparison include the following:

Algorithm: Needleman and Wunsch, *J. Mol. Bio.*, 48:443–453 (1970)

Comparison matrix: matches—+10; mismatches=0

Gap Penalty: 50

Gap Length Penalty: 3

As used herein, "% identity" is determined using the above parameters as the default parameters for nucleic acid molecule sequence comparisons and the "gap" program from GCG, version 10.2.

The invention further relates to nucleic acid molecules that hybridize to nucleic acid molecules of the present invention. In particular, the invention relates to nucleic acid molecules that hybridize under stringent conditions to the above-described nucleic acid molecules. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook et al., Molecular Cloning: A Laboratory Manual, Second Edition, Cold Spring Harbor, N.Y. (1989), particularly Chapter 11.

In embodiments where nucleic acid sequences which when expressed are capable of selectively reducing the level of a protein and/or transcript encoded by a FAD2-1 gene and the level of a protein and/or transcript encoded by at least one FAD3 gene while leaving the level of a protein and/or transcript of a FAD2-2 gene in the plant partially, substantially or essentially unaffected, preferred FAD2-1 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing the level of a protein and/or transcript encoded by a FAD2-2 gene and the level of a protein and/or transcript encoded by at least one FAD3 gene while leaving the level of a protein and/or transcript of a FAD2-1 gene in the plant partially, substantially or essentially unaffected, preferred FAD2-2 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence of SEQ ID NO:4 and fragments thereof, where such a nucleic acid sequence does not hybridize under stringent conditions to a nucleic acid molecule with a nucleotide sequence selected from the group consisting of SEQ ID NO:1 and SEQ ID NO:2; (2) nucleic acid molecules which contain sequences that are also found in a soybean FAD2-2 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing a FAD3 gene, preferred FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5–14, and fragments thereof, where such a nucleic acid sequence does not hybridize under stringent conditions to a nucleic acid molecule with a nucleotide sequence selected from the group consisting of SEQ ID NO: 1, SEQ ID NO:2, and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

One subset of the nucleic acid molecules of the invention includes fragment nucleic acid molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 contiguous nucleotide residues and more preferably, about 15 to about 30 contiguous nucleotide residues, or about 50 to about 100 contiguous nucleotide residues, or about 100 to about 200 contiguous nucleotide residues, or about 200 to about 400 contiguous nucleotide residues, or about 275 to about 350 contiguous nucleotide residues).

In another aspect, a fragment nucleic acid molecule has a nucleic acid sequence that is at least 15, 25, 50, or 100 contiguous nucleotides of a nucleic acid molecule of the present invention. In a preferred embodiment, the nucleic acid molecule has a nucleic acid sequence that is at least 15, 25, 50, or 100 contiguous nucleotides of a nucleic acid molecule having a nucleic acid sequence selected from the group consisting of SEQ ID NO:1 through SEQ ID NO:14 and complements thereof.

A fragment of one or more of the nucleic acid molecules of the present invention may be a probe and specifically a PCR probe. A PCR probe is a nucleic acid molecule capable of initiating a polymerase activity while in a double-stranded structure with another nucleic acid molecule. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112–123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs:1–14, and complements thereof.

As used herein, two nucleic acid molecules are said to be capable of specifically hybridizing to one another if the two molecules are capable of forming an anti-parallel, double-stranded nucleic acid structure.

A nucleic acid molecule of the invention can also encode a homolog nucleic acid molecule. As used herein, a homolog nucleic acid molecule or fragment thereof is a counterpart nucleic acid molecule or fragment thereof in a second species (e.g., corn FAD2-1 intron nucleic acid molecule is a homolog of Arabidopsis FAD2-1 intron nucleic acid molecule). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is obtained from a plant selected from the group consisting of alfalfa, *Arabidopsis*, barley, *Brassica campestris*, oilseed rape, broccoli, cabbage, canola, citrus, cotton, garlic, oat, *Allium*, flax, an ornamental plant, jojoba, corn, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, *Phaseolus*, crambe, mustard, castor bean, sesame, cottonseed, linseed, safflower, and oil palm. More particularly, a preferred homolog is obtained from a plant selected from the group consisting of canola, corn, *Brassica campestris*, oilseed rape, soybean, crambe, mustard, castor bean, peanut, sesame, cottonseed, linseed, rapeseed, safflower, oil palm, flax, and sunflower. In an even more preferred embodiment, the homolog is obtained from a plant selected from the group consisting of canola, rapeseed, corn, *Brassica campestris*, oilseed rape, soybean, sunflower, safflower, oil palm, and peanut.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant or plant part. Exogenous genetic material is any genetic material, whether naturally occurring or otherwise, from any source that is capable of being inserted into any organism.

A plant can have a family of more than one FAD2 or FAD3 genes (i.e., genes which encode an enzyme with the specified activity present at different locations within the genome of the plants). As used herein, a "FAD2 gene family member" is any FAD2 gene found within the genetic material of the plant. As used herein, a "FAD3 gene family member" is any FAD3 gene found within the genetic material of the plant. In one embodiment, a gene family can be additionally classified by the similarity of the nucleic acid sequences. In a preferred aspect of this embodiment, a gene family member exhibits at least 60%, more preferably at least 70%, more preferably at least 80% nucleic acid sequence identity in the coding sequence portion of the gene.

In one embodiment of the invention, the expression level of a protein or transcript in one family member of that gene is selectively reduced while leaving the level of a protein or transcript of a second family member partially unaffected. In a preferred embodiment of the invention, the expression level of a protein or transcript in one family member of that gene is selectively reduced while leaving the level of a protein or transcript of a second family member substantially unaffected. In a highly preferred embodiment of the invention, the expression level of a protein or transcript in one family member of that gene is selectively reduced while leaving the level of a protein or transcript of a second family member essentially unaffected.

In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant partially unaffected. In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant substantially unaffected. In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant essentially unaffected.

In a more particularly preferred embodiment, a soybean plant of the present, invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant partially unaffected. In a more particularly preferred embodiment, a soybean plant of the present invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant substantially unaffected. In a more particularly preferred embodiment, a soybean plant of the present invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant essentially unaffected.

In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant partially unaffected. In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant substantially unaffected. In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant essentially unaffected.

In a preferred embodiment, a soybean of the present invention includes exogenous nucleic acid sequences selected from the groups consisting of a FAD3 intron or fragment thereof, more preferably from a nucleic acid molecule selected from the group consisting of SEQ ID NOs: 5–14, or fragments thereof.

In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant partially unaffected. In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant substantially unaffected. In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant essentially unaffected.

In embodiments where nucleic acid sequences which when expressed are capable of selectively reducing the expression level of a protein and/or transcript encoded by a FAD2-1 gene and at least one FAD3 genes while leaving the level of a protein and/or transcript of a FAD2-2 gene in the plant partially unaffected, substantially unaffected, or essentially unaffected, preferred FAD2-1 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing the expression level of a protein and/or transcript encoded by a FAD3 gene, preferred FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5–14, and fragments thereof, where such a nucleic acid sequence does not hybridize under stringent conditions to a nucleic acid molecule with a nucleotide sequence selected from the group consisting of SEQ ID NO:1, SEQ ID NO:2, and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In a preferred embodiment, a soybean seed of the present invention has an oil composition that is 50% or greater oleic acid and 10% or less linolenic acid. In a more preferred embodiment, a soybean seed of the present invention has an oil composition that is 60% or greater oleic acid and 7% or less linolenic acid. In a particular preferred embodiment, a soybean seed of the present invention has an oil composition that is 65% or greater oleic acid and 5% or less linolenic acid, preferably 4% or less linolenic acid, and more preferably 3% or less linolenic acid. As used herein, all % composition of oils within a plant or plant part such as a seed are determined by relative mole percent.

In another preferred embodiment a soybean seed of the present invention has an oil composition that is between 50% and 90% oleic acid, and 10% or less linolenic acid. In a more preferred embodiment, a soybean seed of the present invention has an oil composition that is between 60% and 80% oleic acid, and 7% or less linolenic acid. In a particular preferred embodiment, a soybean seed of the present invention has an oil composition that is between 65% and 75% oleic acid, and 5% or less linolenic acid, preferably 4% or less linolenic acid, and more preferably 3% or less linolenic acid.

In a particularly preferred embodiment, a soybean seed of the present invention has an oil composition that is between 65% and 75% oleic acid, and 5% or less linolenic acid, preferably 4% or less linolenic acid, and more preferably 3% or less linolenic acid, where nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant partially unaffected, substantially unaffected, or essentially unaffected, the FAD2-1 nucleic acid sequences are selected from the groups consisting of: (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2); and the FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5–14, and fragments thereof, where such a nucleic acid sequence does not hybridize under stringent conditions to a nucleic acid molecule with a nucleotide sequence selected from the group consisting of SEQ ID NO:1, SEQ ID NO:2 and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In another embodiment, a soybean seed of the present invention has an oil composition that is 80% or greater, more preferably 90% or greater oleic acid and 5% or less linolenic acid, preferably 4% or less linolenic acid, and more preferably 3% or less linolenic acid.

In a preferred embodiment, a soybean seed of the present invention has an oil composition that is 80% or greater, more preferably 90% or greater oleic acid and 5% or less linolenic acid, preferably 4% or less linolenic acid, and more preferably 3% or less linolenic acid, where the nucleic acid sequences are capable of reducing the expression of FAD2-1, FAD2-2 and at least one FAD3 genes. In a particularly preferred embodiment of this aspect, the nucleic acid sequences are selected from the group consisting of SEQ ID NO:1 through SEQ ID NO:14 and complements thereof.

In a preferred embodiment of the present invention, a soybean seed of the present invention has an oil composition of 50% or greater oleic acid, more preferably 60% or greater, 70% or greater, 80% or greater, or 90% or greater oleic acid.

In another preferred embodiment of the present invention, a soybean seed of the present invention has an oil composition that is 10% or less linolenic acid, more preferably 5% or less, 4% or less, or 3% or less linolenic acid.

Such genetic material may be transferred into either monocotyledons or dicotyledons including, but not limited to canola, corn, soybean, *Arabidopsis, Phaseolus*, peanut, alfalfa, wheat, rice, oat, sorghum, rapeseed, rye, barley, millet, fescue, perennial ryegrass, sugarcane, cranberry, papaya, banana, safflower, oil palm, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee and dioscorea (Christou, INO: *Particle Bombardment for Genetic Engineering of Plants*, Biotechnology Intelligence Unit. Academic Press, San Diego, Calif. (1996)), with canola, corn, *Brassica campestris*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris*, oilseed rape, soybean, sunflower, safflower, oil palms, and peanut more preferred. In a more preferred embodiment, the genetic material is transferred into canola. In another more preferred embodiment, the genetic material is transferred into oilseed rape. In another particularly preferred embodiment, the genetic material is transferred into soybean.

The levels of products such as transcripts or proteins may be increased or decreased throughout an organism such as a plant or localized in one or more specific organs or tissues of the organism. For example the levels of products may be increased or decreased in one or more of the tissues and organs of a plant including without limitation: roots, tubers, stems, leaves, stalks, fruit, berries, nuts, bark, pods, seeds and flowers. A preferred organ is a seed.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y. (1997)).

A construct or vector may include a plant promoter to express the nucleic acid molecule of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include, but are not limited to, the nopaline synthase (NOS) promoter (Ebert et al., *Proc. Natl. Acad. Sci. (U.S.A.)* 84:5745–5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315–324 (1987)) and the CaMV 35S promoter (Odell et al., *Nature* 313:810–812 (1985)), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624–6628 (1987)), the sucrose synthase promoter (Yang et al., *Proc. Natl. Acad. Sci. (U.S.A.)* 87:4144–4148 (1990)), the R gene complex promoter (Chandler et al., *The Plant Cell* 1:1175–1183 (1989)) and the chlorophyll a/b binding protein gene promoter. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

Particularly preferred promoters can also be used to express a nucleic acid molecule of the present invention in seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos, et al, *Plant Cell,* 1(9):839–853 (1989)), soybean trypsin inhibitor (Riggs, et al., *Plant Cell* 1(6): 609–621 (1989)), ACP (Baerson, et al., *Plant Mol. Biol.,* 22(2):255–267 (1993)), stearoyl-ACP desaturase (Slocombe, et al., *Plant Physiol.* 104(4):167–176 (1994)), soybean a' subunit of b-conglycinin (soy 7s, (Chen et al., *Proc. Natl. Acad. Sci.,* 83:8560–8564 (1986))), and oleosin (see, for example, Hong, et al., *Plant Mol. Biol.,* 34(3):549–555 (1997)). Further examples include the promoter for β-conglycinin (Chen et al., *Dev. Genet.* 10:112–122 (1989)) and the promoter for FAE (PCT Publication WO 01/11061). Preferred promoters for expression in the seed are 7S and napin promoters.

Also included are the zein promoters, which are a group of storage proteins found in corn endosperm. Genomic clones for zein genes have been isolated (Pedersen et al., *Cell* 29:1015–1026 (1982), and Russell et al., *Transgenic Res.* 6(2):157–168) and the promoters from these clones, including the 15 kD, 16 kD, 19 kD, 22 kD, and 27 kD genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.* 13:5829–5842 (1993)). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Tissue-specific expression of a protein of the present invention is a particularly preferred embodiment. The tissue-specific promoters that can be used include the chloroplast glutamine synthetase GS2 promoter from pea (Edwards et al., *Proc. Natl. Acad. Sci. (U.S.A.)* 87:3459–3463 (1990)), the chloroplast fructose-1,6-biphosphatase (FBPase) promoter from wheat (Lloyd et al., *Mol. Gen. Genet.* 225: 209–216 (1991)), the nuclear photosynthetic ST-LS1 promoter from potato (Stockhaus et al., *EMBO J.* 8:2445–2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773–778 (1994)), the promoter for the Cab-1 gene from wheat (Fejes et al., *Plant Mol. Biol.* 15:921–932 (1990)), the promoter for the CAB-1 gene from spinach (Lubberstedt et al., *Plant Physiol.* 104:997–1006 (1994)), the promoter for the cab1R gene from rice (Luan et al., *Plant Cell.* 4:971–981 (1992)), the pyruvate, orthophosphate dikinase (PPDK) promoter from corn (Matsuoka et al., *Proc. Natl. Acad. Sci.* (*U.S.A.*) 90:9586–9590 (1993)), the promoter for the tobacco Lhcb1*2 gene (Cerdan et al., *Plant Mol. Biol.* 33:245–255 (1997)), the *Arabidopsis thaliana* SUC2 sucrose-H+symporter promoter (Truernit et al., *Planta.* 196:564–570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbB gene from white mustard (*Sinapis alba*; Kretsch et al., *Plant Mol. Biol.* 28:219–229 (1995)).

A number of promoters for genes with tuber-specific or tuber-enhanced expression are known and can be used, including the class I patatin promoter (Bevan et al., *EMBO J.* 8:1899–1906 (1986); Jefferson et al., *Plant Mol. Biol.* 14:995–1006 (1990)), the promoter for the potato tuber ADPGPP genes, both the large and small subunits, the sucrose synthase promoter (Salanoubat and Belliard, *Gene* 60:47–56 (1987), Salanoubat and Belliard, *Gene* 84:181–185 (1989)), the promoter for the major tuber proteins including the 22 kd protein complexes and protease inhibitors (Hannapel, *Plant Physiol.* 101:703–704 (1993)), the promoter for the granule-bound starch synthase gene (GBSS) (Visser et al., *Plant Mol. Biol.* 17:691–699 (1991)) and other class I and II patatins promoters (Koster-Topfer et al., *Mol. Gen. Genet.* 219:390–396 (1989); Mignery et al., *Gene.* 62:27–44 (1988)).

Root specific promoters may also be used. An example of such a promoter is the promoter for the acid chitinase gene (Samac et al., *Plant Mol. Biol.* 25:587–596 (1994)). Expression in root tissue could also be accomplished by utilizing the root specific subdomains of the CaMV35S promoter that have been identified (Lam et al., *Proc. Natl. Acad. Sci.* (*U.S.A.*) 86:7890–7894 (1989)). Other root cell specific promoters include those reported by Conkling et al. (Conkling et al., *Plant Physiol.* 93:1203–1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977–984 (1989)).

Constructs or vectors may also include, with the region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671–680 (1989); Bevan et al., *Nucleic Acids Res.* 11:369–385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183–1200 (1987)), the sucrose synthase intron (Vasil et al., *Plant Physiol.* 91:1575–1579 (1989)) and the TMV omega element (Gallie et al., *The Plant Cell* 1:301–311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183–188 (1985)), which codes for kanamycin resistance and can be selected for using kanamycin, RptII, G418, hpt; a bar gene which codes for bialaphos resistance; a mutant EPSP synthase gene (Hinchee et al., *Bio/Technology* 6:915–922 (1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., *Mol. Gen. Genet.* (1987)),) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (European Patent Application 154,204 (Sep. 11, 1985)), ALS (D'Halluin et al., Bio/Technology 10:309–314 (1992)), and a methotrexate resistant DHFR gene (Thillet et al., *J. Biol. Chem.* 263:12500–12508 (1988)).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5:387–405 (1987); Jefferson et al., *EMBO J.* 6:3901–3907 (1987)); an R-locus gene, which encodes a product that regulates the production of anthocyanin pigments (red color) in plant tissues (Dellaporta et al., Stadler Symposium 11:263–282 (1988)); a β-lactamase gene (Sutcliffe et al., *Proc. Natl. Acad. Sci.* (*U.S.A.*) 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)); a xy/E gene (Zukowsky et al., *Proc. Natl. Acad. Sci.* (*U.S.A.*) 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

It is understood that two or more nucleic molecules of the present invention may be introduced into a plant using a single construct and that construct can contain more than one promoter. In embodiments where the construct is designed to express two nucleic acid molecules, it is preferred that the two promoters are (i) two constitutive promoters, (ii) two seed-specific promoters, or (iii) one constitutive promoter and one seed-specific promoter. Preferred seed-specific and constitutive promoters are a napin and a CaMV promoter, respectively. Illustrative combinations are set forth in Example 7. It is understood that two or more of the nucleic molecules may be physically linked and expressed utilizing a single promoter, preferably a seed-specific or constitutive promoter.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, and the like. (Potrykus, *Ann. Rev. Plant Physiol. Plant Mol. Biol.* 42:205–225 (1991); Vasil, *Plant Mol. Biol.* 25:925–937 (1994)). For example, electroporation has been used to transform corn protoplasts (Fromm et al., *Nature* 312:791–793 (1986)).

Other vector systems suitable for introducing transforming DNA into a host plant cell include but are not limited to binary artificial chromosome (BIBAC) vectors (Hamilton et al., *Gene* 200,107–116 (1997)); and transfection with RNA viral vectors (Della-Cioppa et al., *Ann. N.Y. Acad. Sci.* (1996), 792 (Engineering Plants for Commercial Products and Applications), 57–61). Additional vector systems also include plant selectable YAC vectors such as those described in Mullen et al., *Molecular Breeding* 4:449–457 (1988).

Technology for introduction of DNA into cells is well known to those of skill in the art. Four general methods for delivering a gene into cells have been described: (1) chemical methods (Graham and van der Eb, *Virology* 54:536–539 (1973)); (2) physical methods such as microinjection (Capecchi, *Cell* 22:479–488 (1980)), electroporation (Wong and Neumann, *Biochem. Biophys. Res. Commun.* 107:584–587 (1982); Fromm et al., *Proc. Natl. Acad. Sci. (U.S.A.)* 82:5824–5828 (1985); U.S. Pat. No. 5,384,253); the gene gun (Johnston and Tang, *Methods Cell Biol.* 43:353–365 (1994)); and vacuum infiltration (Bechtold et al., *C.R. Acad. Sci. Paris, Life Sci.* 316:1194–1199. (1993)); (3) viral vectors (Clapp, *Clin. Perinatol.* 20:155–168 (1993); Lu et al., *J. Exp. Med.* 178:2089–2096 (1993); Eglitis and Anderson, *Biotechniques* 6:608–614 (1988)); and (4) receptor-mediated mechanisms (Curiel et al., *Hum. Gen. Ther.* 3: 147–154 (1992), Wagner et al., *Proc. Natl. Acad. Sci. (USA)* 89:6099–6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994)). Non-biological particles (microprojectiles) may be coated with nucleic acid molecules and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671–674 (1988)) nor the susceptibility to *Agrobacterium* infection is required. An illustrative embodiment of a method for delivering DNA into corn cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603–618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.)(Sanford et al., *Technique* 3:3–16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example the methods described by Fraley et al., Bio/Technology 3:629–635 (1985) and Rogers et al., Methods Enzymol. 153:253–277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., Mol. Gen. Genet. 205:34 (1986)).

Modern Agrobacterium transformation vectors are capable of replication in E. coli as well as Agrobacterium, allowing for convenient manipulations as described (Klee et al., In: Plant DNA Infectious Agents, Hohn and Schell (eds.), Springer-Verlag, New York, pp. 179–203 (1985)). Moreover, technological advances in vectors for Agrobacterium-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., Methods Enzymol. 153:253–277 (1987)). In addition, Agrobacterium containing both armed and disarmed Ti genes can be used for the transformations. In those plant strains where Agrobacterium-mediated transformation is efficient, it is the method of choice because of the facile and defined nature of the gene transfer.

A transgenic plant formed using Agrobacterium transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

In a preferred embodiment, a plant of the present invention that includes nucleic acid sequences which when expressed are capable of selectively reducing a FAD2 gene is mated with another plant of the present invention that includes nucleic acid sequences which when expressed are capable of selectively reducing a FAD3 gene.

Transformation of plant protoplasts can be achieved using methods based on calcium phosphate precipitation, polyethylene glycol treatment, electroporation and combinations of these treatments (See, for example, Potrykus et al., Mol. Gen. Genet. 205:193–200 (1986); Lorz et al., Mol. Gen. Genet. 199:178 (1985); Fromm et al., Nature 319:791 (1986); Uchimiya et al., Mol. Gen. Genet. 204:204 (1986); Marcotte et al., Nature 335:454–457 (1988)).

Application of these systems to different plant strains depends upon the ability to regenerate that particular plant strain from protoplasts. Illustrative methods for the regeneration of cereals from protoplasts are described (Fujimura et al., Plant Tissue Culture Letters 2:74 (1985); Toriyama et al., Theor. Appl. Genet. 205:34 (1986); Yamada et al., Plant Cell Rep. 4:85 (1986); Abdullah et al., Biotechnology 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, Biotechnology 6:397 (1988)). In addition, "particle gun" or high-velocity microprojectile technology can be utilized (Vasil et al., Bio/Technology 10:667 (1992)).

Using the latter technology, DNA is carried through the cell wall and into the cytoplasm on the surface of small metal particles as described (Klein et al., Nature 328:70 (1987); Klein et al., Proc. Natl. Acad. Sci. (U.S.A.) 85:8502–8505 (1988); McCabe et al., Bio/Technology 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., Intern Rev. Cytol. 107:367 (1987); Luo et al., Plant Mol Biol. Reporter 6:165 (1988)), by direct injection of DNA into reproductive organs of a plant (Pena et al., Nature 325:274 (1987)), or by direct injection of DNA into the cells of immature embryos followed by the rehydration of desiccated embryos (Neuhaus et al., Theor. Appl. Genet. 75:30 (1987)).

The regeneration, development and cultivation of plants from single plant protoplast transformants or from various transformed explants is well known in the art (Weissbach and Weissbach, In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of Agrobacterium tumefaciens and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et al., *Biotechnology* 6:923 (1988); Christou et al., *Plant Physiol.* 87:671–674 (1988)); Brassica (U.S. Pat. No. 5,463, 174); peanut (Cheng et al., *Plant Cell Rep.* 15:653–657 (1996), McKently et al., *Plant Cell Rep.* 14:699–703 (1995)); papaya; pea (Grant et al., *Plant Cell Rep.* 15:254–258 (1995)); and *Arabidopsis thaliana* (Bechtold et al., *C.R. Acad. Sci. Paris, Life Sci.* 316:1194–1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987)); barley (Wan and Lemaux, *Plant Physiol* 104:37 (1994)); corn (Rhodes et al., *Science* 240: 204 (1988); Gordon-Kamm et al., *Plant Cell* 2:603–618 (1990); Fromm et al., *Bio/Technology* 8:833 (1990); Koziel et al., *Bio/Technology* 11:194 (1993); Armstrong et al., *Crop Science* 35:550–557 (1995)); oat (Somers et al, *Bio/Technology* 10:1589 (1992)); orchard grass (Horn et al., *Plant Cell Rep.* 7:469 (1988)); rice (Toriyama et al., *Theor. Appl. Genet.* 205:34 (1986); Part et al., *Plant Mol. Biol.* 32:1135–1148 (1996); Abedinia et al., *Aust. J. Plant Physiol.* 24:133–141 (1997); Zhang and Wu, *Theor. Appl. Genet.* 76:835 (1988); Zhang et al., *Plant Cell Rep.* 7:379 (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)). Transient expression systems may be used to functionally dissect gene constructs (see generally, Maliga et al., *Methods in Plant Molecular Biology*, Cold Spring Harbor Press (1995)).

Any of the nucleic acid molecules of the invention may be introduced into a plant cell in a permanent or transient manner in combination with other genetic elements, for example, including but not limited to, vectors, promoters, and enhancers. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279–289 (1990); van der Krol et al., *Plant Cell* 2:291–299 (1990)). Cosuppression may result from stable transformation with a single copy nucleic acid molecule that is homologous to a nucleic acid sequence found with the cell (Prolls and Meyer, *Plant J.* 2:465–475 (1992)) or with multiple copies of a nucleic acid molecule that is homologous to a nucleic acid sequence found with the cell (Mittlesten et al., *Mol. Gen. Genet.* 244:325–330 (1994)). Genes, even though different, linked to homologous promoters may result in the cosuppression of the linked genes (Vaucheret, *C.R. Acad. Sci. III* 1316:1471–1483 (1993); Flavell, *Proc. Natl. Acad. Sci.* (*U.S.A.*) 91:3490–3496 (1994)); van Blokland et al., *Plant J.* 6:861–877 (1994); Jorgensen, *Trends Biotechnol.* 8:340–344 (1990); Meins and Kunz, In: *Gene Inactivation and Homologous Recombination in Plants*, Paszkowski (ed.), pp. 335–348, Kluwer Academic, Netherlands (1994))(Kinney, Induced Mutations and Molecular Techniques for Crop Improvement, Proceedings of a Symposium 19–23 Jun. 1995 jointly organized by IAEA and FA)), pages 101–113 (IAEA-SM 340–49).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427–430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49–63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569–597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155–184 (1990)). An antisense vector is constructed by standard procedures and introduced into cells by methods including but not limited to transformation, transfection, electroporation, microinjection, and infection. The type of transformation and choice of vector will determine whether expression is transient or stable. The promoter used for the antisense gene may influence the level, timing, tissue, specificity, or inducibility of the antisense inhibition.

It has been reported that the introduction of double-stranded RNA into cells may also be used to disrupt the function of an endogenous gene. (Fire et al., *Nature* 391: 806–811 (1998)). Such disruption has been demonstrated, for example, in *Caenorhabditis elegans* and is often referred to as RNA interference, or RNAi. (Fire et al., *Nature* 391:806–811 (1998)). The disruption of gene expression in *C. elegans* by double-stranded RNA has been reported to induce suppression by a post-transcriptional mechanism. (Montgomery et al., Proc. Natl. Acad. Sci. 95:15502–15507 (1998)). Evidence of gene silencing by double-stranded RNA has also been reported for plants. (Waterhouse et al., *Proc. Natl. Acad. Sci.* 95:13959–13964 (1998)).

An intron-spliced hairpin structure reportedly may also be used to effect post-transcriptional gene suppression. (Smith et al., *Nature* 407:319–320 (2000)). Reports indicate that post-transcriptional gene silencing can be induced with almost 100% efficiency by the use of intron-spliced RNA with a hairpin structure. (Smith et al., *Nature* 407:319–320 (2000)).

It is understood that one or more of the nucleic acids of the invention may be modified in order to effect RNAi or another mode of post-transcriptional gene suppression.

The present invention also provides for parts of the plants, particularly reproductive or storage parts. Plant parts, without limitation, include seed, endosperm, ovule, pollen, roots, tubers, stems, leaves, stalks, fruit, berries, nuts, bark, pods, seeds and flowers. In a particularly preferred embodiment of the present invention, the plant part is a seed.

The present invention also provides a container of over 10,000, more preferably 20,000, and even more preferably 40,000 seeds where over 10%, more preferably 25%, more preferably 50% and even more preferably 75% or 90% of the seeds are seeds derived from a plant of the present invention.

The present invention also provides a container of over 10 kg, more preferably 25 kg, and even more preferably 50 kg seeds where over 10%, more preferably 25%, more preferably 50% and even more preferably 75% or 90% of the seeds are seeds derived from a plant of the present invention.

Any of the plants or parts thereof of the present invention may be processed to produce a feed, meal, protein, or oil preparation. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

In one embodiment, an oil of the present invention has an oil composition that is 50% or greater oleic acid and 10% or less linolenic acid. In another embodiment, an oil of the present invention has an oil composition that is 60% or greater oleic acid and 7% or less linolenic acid. In another embodiment, an oil of the present invention has an oil composition that is 65% or greater oleic acid and 5% or less linolenic acid, preferably 4% or less linolenic acid, and more preferably 3% or less linolenic acid.

In another embodiment, an oil of the present invention has an oil composition that is between 50% and 90% oleic acid and 10% or less linolenic acid. In another embodiment, an oil of the present invention has an oil composition that is between 60% and 80% oleic acid and 7% or less linolenic acid. In another embodiment, an oil of the present invention has an oil composition that is between 65% and 75% oleic acid and 5% or less linolenic acid, preferably 4% or less linolenic acid, and more preferably 3% or less linolenic acid.

In another embodiment, an oil of the present invention has an oil composition that is 80% or greater, more preferably 90% or greater oleic acid and 5% or less linolenic acid, preferably 4% or less linolenic acid, and more preferably 3% or less linolenic acid. In another embodiment, an oil of the present invention has an oil composition that is 50% or greater oleic acid, more preferably 60% or greater, 70% or greater, 80% or greater, or 90% or greater oleic acid. In another embodiment, an oil of the present invention has an oil composition that is 10% or less linolenic acid, preferably 5% or less, 4% or less, or 3% or less linolenic acid.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2–3 (1987))).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Computer Readable Medium

The nucleotide sequence provided in SEQ ID NO:1 through 15, 18, 19, 22, 23, or fragment thereof or complement thereof, or a nucleotide sequence at least 50%, 60%, or 70% identical, preferably 80%, 85% identical, or especially preferably 90%, or 95% identical, or particularly highly preferably 97%, 98%, or 99% identical to the sequence provided in SEQ ID NO:1 through 15, 18, 19, 22, 23, or fragment thereof or complement thereof, can be "provided" in a variety of media to facilitate use. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy disk, hard disc, storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising a computer readable medium having recorded thereon a nucleotide sequence of the present invention.

As used herein, "recorded" refers to a process for storing information on computer readable medium. A skilled artisan can readily adopt any of the presently known methods for recording information on computer readable media to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as Word Perfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable media having recorded thereon the nucleotide sequence information of the present invention.

By providing one or more nucleotide sequences of the present invention, a skilled artisan can routinely access the sequence information for a variety of purposes. Computer software is publicly available which allows a skilled artisan to access sequence information provided in a computer readable medium. Software which implements the BLAST (Altschul et al., *J. Mol. Biol.* 215:403–410 (1990)) and BLAZE (Brutlag et al., *Comp. Chem.* 17:203–207 (1993), the entirety of which is herein incorporated by reference) search algorithms on a Sybase system can be used to identify non-coding regions and other nucleic acid molecules of the present invention within the genome that contain homology to non-coding regions from other organisms. Such non-coding regions may be utilized to affect the expression of commercially important proteins such as enzymes used in amino acid biosynthesis, metabolism, transcription, translation, RNA processing, nucleic acid and protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecules of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems is suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTIN, and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, the target sequence may be of shorter length.

As used herein, "a target structural motif," or "target motif" refers to any rationally selected sequence or combination of sequences in which the sequences are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures, and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software that implement the BLAST and BLAZE algorithms (Altschul et al., *J. Mol. Biol.* 215:403–410 (1990)) can be used to identify non-coding regions within the nucleic acid molecules of the present invention. A skilled artisan can readily recognize that any one of the publicly available homology search programs can be used as the search means for the computer-based systems of the present invention.

The following examples are illustrative and not intended to be limiting in any way.

EXAMPLES

Example 1

Cloning of Desaturase Genomic Sequences

1A. Soybean Δ12 Desaturase (FAD2-1)

A soybean FAD2-1A sequence is identified by screening a soybean genomic library using a soybean FAD2-1 cDNA probe. Three putative soy FAD2-1 clones are identified and plaque purified. Two of the three soy FAD2-1 clones are ligated into pBluescript II KS+ (Stratagene) and sequenced. Both clones (14-1 and 11-12) are the same and match the soy FAD2-1 cDNA exactly. A sequence of the entire FAD2-1A clone is provided in SEQ ID NO:15.

Prior to obtaining a full length clone, a portion of the FAD2-1A genomic clone is PCR amplified using PCR primers designed from the 5' untranslated sequence (Primer 12506, 5'-ATACAA GCCACTAGGCAT-3', SEQ ID NO:16) and within the cDNA (Primer 11698: 5'-GATTGGCCATG-CAATGAGGGAAAAGG-3', SEQ ID NO:17). The resulting PCR product is cloned into the vector pCR 2.1 (Invitrogen) and sequenced. A soy FAD2-1A partial genomic clone (SEQ ID NO:18) with an intron region (SEQ ID NO:1) is identified by comparison to the soybean cDNA sequence using the Pustell comparison program in Macvector. The FAD2-1A intron sequence (SEQ ID NO:1) begins after the ATG start codon, and is 420 bases long.

A second FAD2-1 gene family member is also identified and cloned, and is referred to herein as FAD2-1B. The soy FAD2-1B partial genomic clone (SEQ ID NO:19) has a coding region (base pairs 1783–1785 and 2191–2463) and an intron region (base pairs 1786–2190) which are identified by comparison to the soybean cDNA sequence using the Pustell comparison program in Macvector. The FAD2-1B intron sequence (SEQ ID NO:2) begins after the ATG start codon and is 405 bases long. Other regions in the FAD2-1B partial genomic clone (SEQ ID NO:19) include a promoter (base pairs 1–1704) (SEQ ID NO:22) and 5'UTR (base pairs 1705–1782).

1B. Soybean Δ15 Desaturase (FAD3)

A partial soybean FAD3-1A genomic sequence is PCR amplified from soybean DNA using primers 10632, 5'-CUACUACUACUACTCGAGACAAAGCCTT-TAGCCTATG-3' (SEQ ID NO:20), and 10633: 5'-CAU-CAUCAUCAUGGATCCCATGTCTCTCTATGCAAG-3' (SEQ ID NO:21). The Expand Long Template PCR system (Boehringer Mannheim) is used according to the manufacturer's directions. The resulting PCR products are cloned into the vector pCR 2.1 (Invitrogen) and sequenced. A soy FAD3-1A partial genomic clone sequence (SEQ ID NO:23) and intron regions are confirmed by comparisons to the soybean FAD3-1A cDNA sequence using the Pustell program in Macvector.

From the identified partial genomic soybean FAD3-1A sequence (SEQ ID NO:23), seven introns are identified: FAD3-1A intron #1(SEQ ID NO:5), FAD3-1A intron #2 (SEQ ID NO:6), FAD3-1A intron #3A (SEQ ID NO:7), FAD3-1A intron #4 (SEQ ID NO:8), FAD3-1A intron #5 (SEQ ID NO:9), FAD3-1A intron #3B (SEQ ID NO:10), and FAD3-1A intron #3C (SEQ ID NO:11). FAD3-1A Intron #1 is 192 base pairs long and is located between positions 294 and 485, FAD3-1A intron #2 is 348 base pairs long and is located between positions 576 and 923, FAD3-1A intron #3A is 142 base pairs long and is located between positions 991 and 1132, FAD3-1A intron #3B is 98 base pairs long and is located between positions 1225 and 1322, FAD3-1A intron #3C is 115 base pairs long and is located between positions 1509 and 1623, FAD3-1A intron #4 is 1231 base pairs long and is located between positions 1705 and 2935, and FAD3-1A intron #5 is 626 base pairs long and is located between positions 3074 and 3699.

Example 2

Expression Constructs

The FAD2-1A intron sequence (SEQ ID NO:1) is amplified via PCR using the FAD2-1A partial genomic clone (SEQ ID NO:18) as a template and primers 12701(5'-ACGAATTCCTCGAGGTAAA TTAAATTGTGCCTGC-3' (SEQ ID NO:24)) and 12702 (5'-GCGAGATCTATCG ATCTGTGTCAAAGTATAAAC-3' (SEQ ID NO:25)). The resulting amplification products are cloned into the vector pCR 2.1 (Invitrogen) and sequenced. The FAD2-1A intron is then cloned into the expression cassette, pCGN3892, in sense and antisense orientations. The vector pCGN3892 contains the soybean 7S promoter and a pea RBCS 3'. Both gene fusions are then separately ligated into pCGN9372, a vector that contains the CP4 gene regulated by the FMV promoter. The resulting expression constructs (pCGN5469 sense and pCGN5471 antisense) are used for transformation of soybean using biolistic methods described below.

The FAD2-1B intron sequence (SEQ ID NO:2) is amplified via PCR using the FAD2-1B partial genomic clone (SEQ ID NO:19) as a template and primers 13883 (5'-GCGATCGATGTATGATGCTAAATTAAATTGTGCCTG-3' (SEQ ID NO:28)) and 13876 (5'-GCGGAATTCCTGT-GTCAAAGTATAAAGAAG-3' (SEQ ID NO:29)). The resulting amplification products are cloned into the vector pCR 2.1 (Invitrogen) and sequenced. The FAD2-1B intron is fused to the 3' end of the FAD2-1A intron in plasmids pCGN5468 (contains the soybean 7S promoter fused to the FAD2-1A intron (sense) and a pea RBCS 3') or pCGN5470 (contains the soybean 7S promoter fused to the FAD2-1A intron (antisense) and a pea RBCS 3') in sense or antisense orientation respectively. The resulting intron combo fusions are then ligated separately into pCGN9372, a vector that contains the CP4 gene regulated by the FMV promoter. The resulting expression constructs (pCGN5485, FAD2-1A & FAD2-1B intron sense and pCGN5486, FAD2-1A & FAD2-1B intron antisense) are used for transformation of soybean using biolistic methods described below.

Four of the seven introns identified from the soybean FAD3-1A genomic clone are PCR amplified using the FAD3-1A partial genomic clone as template and primers as follows: FAD3-1A Intron #1, primers 12568: 5'-GATCGAT-GCCCGGGGTAATAATTTTTGTGT-3' (SEQ ID NO:30) and 12569: 5'-CACGCCTCGAGTGTTCAATTCAAT-CAATG-3' (SEQ ID NO:31); FAD3-1A Intron #2, primers 12514: 5'-CACTCGAGTTAGTTCATACTGGCT-3' (SEQ ID NO:32) and 12515: 5'-CGCATCGATTGCAAAATC-CATCAAA-3' (SEQ ID NO:33); FAD3-1A Intron #4, primers 10926: 5'-CUACUACUACUACTCGAGCGTAAAT-AGTGGGTGAACAC-3' (SEQ ID NO:34) and 10927:5'-CAUCAUCAUCAUCTCGAGGAATTCGTCCATTTTAGT ACACC-3' (SEQ ID NO:35); FAD3-1A Intron #5, primers 10928: 5'-CUACUACUACUACTCGAGGCGCGT ACATTTTATTGCTTA-3' (SEQ ID NO:36) and 10929: 5'-CAUCAUCAUCAUCT CGAGGAATTCTGCAGT-GAATCCAAATG-3' (SEQ ID NO:37). The resulting PCR products for each intron are cloned into the vector pCR 2.1 (Invitrogen) and sequenced.

FAD3-1A introns #1, #2, #4 and #5 are all ligated separately into the pCGN3892, in sense or antisense orientations. pCGN3892 contains the soybean 7S promoter and a pea RBCS 3'. These fusions are ligated into pCGN9372, a vector that contains the CP4 gene regulated by the FMV promoter for transformation into soybean. The resulting expression constructs (pCGN5455, FAD3-1A intron #4 sense; pCGN5459, FAD3-1A intron #4 antisense; pCGN5456, FAD3 intron #5 sense; pCGN5460, FAD3-1A intron #5 antisense; pCGN5466, FAD3-1A intron #2 antisense; pCGN5473, FAD3-1A intron #1 antisense) are used for transformation of soybean using biolistic methods described below.

Introns #3C and #4 are also PCR amplified from a second FAD3 gene family member (FAD3-1B). Soybean FAD3-1B introns #3C and #4 are PCR amplified from soybean DNA using the following primers, 5'CATGCTTTCTGTGCT-TCTC 3' (SEQ ID NO:26) and 5' GTTGATCCAACCAT-AGTCG 3' (SEQ ID NO:27). The PCR products are cloned into the vector pCR 2.1 (Invitrogen) and sequenced. A sequence for the FAD3-1B introns #3C and #4 is provided in SEQ ID NOs:12 and 13, respectively.

Example 3

Plant Transformation and Analysis

Linear DNA fragments containing the expression constructs for sense and antisense expression of the Δ12 and Δ15 desaturase introns are stably introduced into soybean (Asgrow variety A4922) by the method of McCabe et al. (1988), *Bio/Technology*, 6:923–926. Transformed soybean plants are identified by selection on media containing glyphosate.

Fatty acid compositions are analyzed from seed of soybean lines transformed with the intron expression constructs using gas chromatography. R1 pooled seed and R1 single seed oil compositions demonstrate that the mono- and polyunsaturated fatty acid, compositions were altered in the oil of seeds from transgenic soybean lines as compared to that of the seed from non-transformed soybean. Table I provides a summary of results which were obtained using the described constructs. These data clearly show that sense and antisense expression of the non-coding regions of the desaturase gene results in the modification of the fatty acid compositions. The data also shows that introns can be used to obtain a variety of lines with varying fatty acid compositions. Selections can be made from such lines depending on the desired relative fatty acid composition. In addition, since each of the introns is able to modify the levels of each fatty acid to varying extends, it is contemplated that combinations of introns can be used depending on the desired compositions.

TABLE I

| FAD2 | Orientation | Event | Oleic | Linoleic | Linolenic |
|---|---|---|---|---|---|
| wildtype (control) | | 5469-5 null R1 pool | 18.15% | 55.59% | 7.97% |
| | | 10 seed average | 13.89% | 55.89% | 9.067% |
| | | 5469-27 null R1 pool | 19.15% | 54.62% | 9.32% |
| | | A4922 | 15.75% | 56.1% | 8.75% |
| | | 5471-13 null R1 pool | 17.02% | 56.49% | 9.08% |
| | | 10 seed average | 13.86% | 56.14% | 9.49% |
| | | A4922 | 14.95% | 55.95% | 9.07% |
| full length cDNA (control) | sense | 5462-133 R1 pool | 84% | 2.17% | 1.55% |
| | | best 5462-133 R1 seed | 84% | 0.59% | 1.76% |
| intron 1 | sense | 5469-6 R1 pool | 29.93% | 46.53% | |
| | | 5469-8 R1 pool | 36.5% | 42.11% | 5.98% |
| | | best 5469-6 R1 seed | 44.41% | 29.34% | 6.68% |
| | | best 5469-8 R1 seed | 41.26% | 33.16% | 5.74% |
| | | 5469-14 R1 pool | 61.06% | 16.42% | 7.75% |
| | | 5469-20 R1 pool | 48.89% | 31.61% | 4.89% |
| | | 5469-22 R1 pool | 80% | 2.97% | 4.78% |
| | | best 5469-14 R1 seed | 62.21% | 11.97% | 8.81% |
| | | 5485-3 R1 pool | 63.54% | 14.09% | 7.32% |
| | | 5485-53 R1 pool | 47.58% | 27.64% | 7.81% |
| | antisense | 5471-8 R1 pool | 31.05% | 43.62% | 7.07% |
| | | 5471-2 R1 pool | 27.98% | 48.88% | 6.83% |
| | | 5471-26 R1 pool | 32.66% | 44.54% | 6.76% |
| | | best 5471-8 R1 seed | 57.4% | 23.37% | 5.73% |
| | | best 5471-2 R1 seed | 28.08% | 46.14% | 6.52% |
| | | best 5471-26 R1 seed | 43.3% | 34.15% | 5.6% |
| | | 5486-33 R1 pool | 32.37% | 43.66% | 6.87% |
| | | 5486-12 R1 pool | 27.32% | 46.97% | 6.4% |
| | | 5486-40 R1 pool | 26.79% | 48.72% | 6.55% |
| FAD3 | | | | | |
| wildtype (control) | | 5473-7 null R1 pool | 15.65% | 56.74% | 9.55% |
| | | A4922 R1 pool | 19.84% | 56.79% | 7.48% |
| full length cDNA (control) | sense | 5464-50 R1 pool | 18.06% | 62.03% | 2.75% |
| | | best 5464-50 R1 seed | 17.08% | 62.44% | 1.72% |
| intron 1 | antisense | 5473-8 R1 pool | 33.47% | 45.97% | 5.54% |
| | | 5473-1 R1 pool | 33.34% | 42.67% | 7.59% |
| intron 2 | antisense | 5466-20 R1 pool | 28.43% | 48.83% | 6.37% |
| | | 5466-16 R1 pool | 27.61% | 49.92% | 5.96% |
| intron 4 | sense | 5455-19 R1 pool | 40.35% | 39.97% | 4.61% |
| | | 5455-10 R1 pool | 35.14% | 43.59% | 5.53% |
| | | 5455-57 R1 pool | 38.04% | 42.44% | 5.24% |
| | | 5455-76 R1 pool | 37.24% | 42.42% | 5.37% |
| | | 5455-107 R1 pool | 36.44% | 42.72% | 5.62% |
| | | best 5455-57 R1 seed | 45.36% | 35.55% | 4.92% |
| | | best 5455-76 R1 seed | 35.3% | 43.54% | 5.53% |
| | | best 5455-107 R1 seed | 45.56% | 34.85% | 5.12% |
| | antisense | 5459-2 R1 pool | 34.5% | 43.87% | 5.59% |
| | | 5459-6 R1 pool | 33.78% | 44.12% | 5.62% |
| | | 5459-20 R1 pool | 28.26% | 49.48% | 5.5% |
| | | best 5459-2 R1 seed | 61.45% | 23.45% | 3.38% |

TABLE I-continued

| FAD2 | Orientation | Event | Oleic | Linoleic | Linolenic |
|---|---|---|---|---|---|
| intron 5 | sense | best 5459-6 R1 seed | 53.51% | 29.68% | 3.53% |
| | | best 5459-20 R1 seed | 30% | 50.55% | 4.15% |
| | | 5456-38 R1 pool | 28.23% | 49.59% | 6.74% |
| | | 5456-62 R1 pool | 28.94% | 48.66% | 6.25% |
| | | best 5456-62 R1 seed | 29.5% | 43.69% | 5.4% |
| | antisense | 5460-9 R1 pool | 29.78% | 48.57% | 5.54% |
| | | 5460-21 R1 pool | 28.37% | 49.79% | 5.54% |
| | | best 5460-21 R1 seed | 35.18% | 40.52% | 5.33% |

Example 4

RNA is isolated from homozygous R2 seed from two FAD2-1 intron suppressed lines (5469-14 and 5469-22), from two FAD2-1 cDNA suppressed lines (positive controls) (5462-87 and 5462-133), and from negative controls (wild type seed and seed from null segregants from each intron suppressed event). Northern gels containing these RNA samples are probed with the FAD2-1 cDNA. FAD2-1A transcript levels are significantly reduced in both the intron suppressed lines and the cDNA suppressed lines relative to the negative controls. The same Northern blot is probed with the constitutive FAD2-2 cDNA and no significant differences in the FAD2-2 transcript levels are observed between the FAD2-1 intron suppressed lines and the controls. In contrast, the FAD2-2 transcript in the cDNA suppressed lines, is significantly reduced. This Northern data indicates that the FAD2-1A intron is specifically inhibiting the accumulation of the FAD2-1 transcript but not the FAD2-2 transcript. A partial FAD2-2 genomic clone (SEQ ID NO:3) is PCR amplified and sequence analysis reveals a 4.7 KB intron in the 5' untranslated region of the gene. The sequence of the FAD2-2 intron (SEQ ID NO:4) shares no homology with the FAD2-1 intron.

Example 5

Southern blot data indicated that there are at least two FAD3 gene family members. To determine the sequence of the other FAD3 gene family member and to determine if other members existed, a FAD3-1A gene sequence is used for a query Blast search against the soybean DNA sequences. Candidate ESTs from different FAD3 gene family members are used to design primers. Using this strategy, 2 primer sets are designed based on putative FAD3 sequences. Intron #4 regions from two other FAD3 gene family members are isolated. Primers are designed from the 211565_1. r1040 EST (designated FAD3-1B), (5' primer #15024: 5'-CATGCTTTCTGTGCTTCTC-3' (SEQ ID NO:26) and 3' primer #15027: 5'-GTTGATCCAACCAT-AGTCG-3' (SEQ ID NO:27)) in the region corresponding to the position of intron #4 of the FAD3-1A gene. These primers are used to PCR amplify the FAD3-1B intron #4 (SEQ ID NO:13), which when sequenced shared no sequence homology with the FAD3-1A intron #4 (SEQ ID NO:8). The FAD3-1B gene also contains an intron #3C (SEQ ID NO:12), which also did not share any homology with the FAD3-1A intron #3C (SEQ ID NO:11).

Another additional intron #4 is PCR amplified from a second EST, gsv701051989. H1 (designated FAD3-1C) using the following set of primers: 5' primer #16241: 5'-CACCATGGTCATCATCAGAAAC (SEQ ID NO:38) and the 3' primer #16242: TCACGATCCACAGTTGT-GAGAC (SEQ ID NO:39). The FAD3-1C intron #4 (SEQ ID NO:14) shares 50% homology with the FAD3-1A intron #4 (SEQ ID NO:8) and shares no homology with the FAD3-1B intron #4 (SEQ ID NO:13). The FAD3-1C EST, like the FAD3-1B EST, also contains an intron #4 splice site in the same region of the gene.

Example 6

Fad2-1A/Fad3-1A Transformed Plants

A soybean FAD2-1A intron suppressed line can be used to pollinate a soybean FAD3-1A intron suppressed line generated according to the methodology set forth in Example 3. RNA from soybean seeds containing both an expressed FAD2-1A intron region and FAD3-1A intron region can be screened using Northern blots (as described in Example 4) to determine the levels of FAD2-1, FAD2-2, FAD3-1A and FAD3-1B transcripts. Soybean plants with undetectable or low levels of FAD2-1 and FAD3-1A transcripts can be screened for fatty acid composition as set forth in Example 3.

Example 7

Single Fad2/Fad3 Constructs

Linear DNA fragments containing sense and antisense FAD2 and FAD3 introns, as well as FAD2 and FAD3 introns capable of producing a dsRNA, can be constructed as set forth in Table II.

TABLE II

| Construct No. | Promoter 1 | Structural Nucleic Acid 1 (sense, antisense, dsRNA) | Promotor 2 | Structural Nucleic Acid 2 (sense, antisense, dsRNA) |
|---|---|---|---|---|
| 1 | CaMV | FAD2-1A intron 1 | CaMV | FAD3-1A intron 1 |
| 2 | CaMV | FAD2-1B intron 1 | CaMV | FAD3-1A intron 1 |
| 3 | CaMV | FAD2-1A intron 1 | CaMV | FAD3-1A intron 4 |
| 4 | CaMV | FAD2-1B intron 1 | CaMV | FAD3-1A intron 4 |

TABLE II-continued

| Construct No. | Promoter 1 | Structural Nucleic Acid 1 (sense, antisense, dsRNA) | Promotor 2 | Structural Nucleic Acid 2 (sense, antisense, dsRNA) |
|---|---|---|---|---|
| 5 | CaMV | FAD2-1A intron 1 | CaMV | FAD3-1B intron 4 |
| 6 | CaMV | FAD2-1B intron 1 | CaMV | FAD3-1B intron 4 |
| 7 | CaMV | FAD2-1A intron 1 | CaMV | FAD3-1C intron 4 |
| 8 | CaMV | FAD2-1B intron 1 | CaMV | FAD3-1C intron 4 |
| 9 | CaMV | FAD2-1A intron 1 | CaMV | FAD2-2B intron 1 |
| 10 | CaMV | FAD2-1B intron 1 | CaMV | FAD2-2B intron 1 |
| 11 | napin | FAD2-1A intron 1 | napin | FAD3-1A intron 1 |
| 12 | napin | FAD2-1B intron 1 | napin | FAD3-1A intron 1 |
| 13 | napin | FAD2-1A intron 1 | napin | FAD3-1A intron 4 |
| 14 | napin | FAD2-1B intron 1 | napin | FAD3-1A intron 4 |
| 15 | napin | FAD2-1A intron 1 | napin | FAD3-1B intron 4 |
| 16 | napin | FAD2-1B intron 1 | napin | FAD3-1B intron 4 |
| 17 | napin | FAD2-1A intron 1 | napin | FAD3-1C intron 4 |
| 18 | napin | FAD2-1B intron 1 | napin | FAD3-1C intron 4 |
| 19 | napin | FAD2-1A intron 1 | napin | FAD2-2B intron 1 |
| 20 | napin | FAD2-1B intron 1 | napin | FAD2-2B intron 1 |
| 21 | 7S | FAD2-1A intron 1 | CaMV | FAD3-1A intron 1 |
| 22 | 7S | FAD2-1B intron 1 | CaMV | FAD3-1A intron 1 |
| 23 | 7S | FAD2-1A intron 1 | CaMV | FAD3-1A intron 4 |
| 24 | 7S | FAD2-1B intron 1 | CaMV | FAD3-1A intron 4 |
| 25 | 7S | FAD2-1A intron 1 | CaMV | FAD3-1B intron 4 |
| 26 | 7S | FAD2-1B intron 1 | CaMV | FAD3-1B intron 4 |
| 27 | 7S | FAD2-1A intron 1 | CaMV | FAD3-1C intron 4 |
| 28 | 7S | FAD2-1B intron 1 | CaMV | FAD3-1C intron 4 |
| 29 | 7S | FAD2-1A intron 1 | CaMV | FAD2-2B intron 1 |
| 30 | 7S | FAD2-1B intron 1 | CaMV | FAD2-2B intron 1 |
| 31 | CaMV | FAD2-1A intron 1 | 7S | FAD3-1A intron 1 |
| 32 | CaMV | FAD2-1B intron 1 | 7S | FAD3-1A intron 1 |
| 33 | CaMV | FAD2-1A intron 1 | 7S | FAD3-1A intron 4 |
| 34 | CaMV | FAD2-1B intron 1 | 7S | FAD3-1A intron 4 |
| 35 | CaMV | FAD2-1A intron 1 | 7S | FAD3-1B intron 4 |
| 36 | CaMV | FAD2-1B intron 1 | 7S | FAD3-1B intron 4 |
| 37 | CaMV | FAD2-1A intron 1 | 7S | FAD3-1C intron 4 |
| 38 | CaMV | FAD2-1B intron 1 | 7S | FAD3-1C intron 4 |
| 39 | CaMV | FAD2-1A intron 1 | 7S | FAD2-2B intron 1 |
| 40 | CaMV | FAD2-1B intron 1 | 7S | FAD2-2B intron 1 |

As shown, each construct listed in the table can have several configurations depending on the nature and orientation of the structural nucleic acids in the construct. For example, construct 30 may be configured as follows: (1) 7S promoter—FAD2-1B intron 1 (sense)—CaMV promoter—FAD2-2B intron 1(sense); (2) 7S promoter—FAD2-1B intron 1 (sense)—CaMV promoter—FAD2-2B intron 1 (antisense); (3) 7S promoter—FAD2-1B intron 1 (sense)—CaMV promoter—FAD2-2B intron 1 (dsRNA); (4) 7S promoter—FAD2-1B intron 1 (antisense)—CaMV promoter—FAD2-2B intron 1 (sense); (5) 7S promoter—FAD2-1B intron 1 (antisense)—CaMV promoter—FAD2-2B intron 1 (antisense); (6) 7S promoter—FAD2-1B intron 1 (antisense)—CaMV promoter—FAD2-2B intron 1 (dsRNA); (7) 7S promoter—FAD2-1B intron 1 (dsRNA)—CaMV promoter—FAD2-2B intron 1 (sense); (8) 7S promoter—FAD2-1B intron 1 (dsRNA)—CaMV promoter—FAD2-2B intron 1 (antisense); or (9) 7S promoter—FAD2-1B intron 1 (dsRNA)—CaMV promoter—FAD2-2B intron 1 (dsRNA).

These constructs can be stably introduced into soybean (for example, Asgrow variety A4922 or Asgrow variety A3244) by the methods described earlier, including the methods of McCabe et al. (1988), *Bio/Technology*, 6:923–926 or *Agrobacterium*-mediated transformation. Transformed soybean plants are identified by selection on media containing glyphosate. Fatty acid compositions are analyzed from seed of soybean lines transformed with the constructs using gas chromatography.

Example 8

Linear DNA fragments containing expression constructs for sense and antisense expression of the FAD2-1 and FAD2-2 introns are stably introduced into soybean (Asgrow variety A4922) by the method of McCabe et al. (1988), *Bio/Technology*, 6:923–926. The following constructs are introduced: (1) FAD2-1A intron (sense)—FAD2-2 intron (antisense); (2) FAD2-1A intron (sense)—FAD2-2 intron (sense); (3) FAD2-1A intron (antisense)—FAD2-2 intron (antisense); (4) FAD2-1A intron (antisense)—FAD2-2 intron (sense); (5) FAD2-1B intron (sense)—FAD2-2 intron (antisense); (6) FAD2-1B intron (sense)—FAD2-2 intron (sense); (7) FAD2-1B intron (antisense)—FAD2-2 intron (antisense); and (8) FAD2-1B intron (antisense)—FAD2-2 intron (sense). Transformed soybean plants are identified by selection on media containing glyphosate. Fatty acid compositions are analyzed from seed of soybean lines transformed with the constructs using gas chromatography. Seed of the transformed plants exhibit high levels of oleic acid (over 80%).

Additional linear DNA fragments containing expression constructs for sense and antisense expression of the FAD2-1, FAD2-2, and FAD3 introns are stably introduced into soybean (Asgrow variety A4922) by the method of McCabe et al. (1988), *Bio/Technology*, 6:923–926. Exemplary constructs include: (1) FAD2-1A intron (sense or antisense)—FAD2-2 intron (sense or antisense)—FAD3-1A intron 1 (sense or antisense); (2) FAD2-1A intron (sense or antisense)—FAD2-2 intron (sense or antisense)—FAD3-1A intron 4 (sense or antisense); (3) FAD2-1A intron (sense or antisense)—FAD2-2 intron (sense or antisense)—FAD3-1B intron 4 (sense or antisense); and (4) FAD2-1A intron (sense or antisense)—FAD2-2 intron (sense or antisense)—FAD3-1C intron 4 (sense or antisense). Transformed soybean plants are identified by selection on media containing glyphosate. Fatty acid compositions are analyzed from seed of soybean lines transformed with the constructs using gas chromatography. Seed of the transformed plants exhibit high levels of oleic acid (over 80%).

All publications and patent applications mentioned in this specification are herein incorporated by reference to the same extent as if each individual publication or patent application was specifically and individually indicated to be incorporated by reference.

What is claimed is:

1. A transformed soybean plant having a nucleic acid molecule that comprises
   (a) a first promoter operably linked to a first nucleic acid molecule having a first nucleic acid sequence that has 90% or greater identity to SEQ ID NO: 1, its complement and fragments of either, wherein said first nucleic acid molecule is capable of suppressing endogenous expression of Fad2-1, and
   (b) a second nucleic acid molecule with a second nucleic acid sequence that has 90% or greater identity to SEQ ID NO: 14, its complement and fragments of either, wherein the second nucleic acid molecule is operable linked to the first promoter or a second promoter, wherein said first nucleic acid molecule is capable of suppressing endogenous expression of Fad3-1.

2. The transformed soybean plant according to claim 1, wherein a single promoter is operably linked to the first and second nucleic acid molecules.

3. The transformed soybean plant according to claim 2, wherein the single promoter is a seed specific promoter.

4. The transformed soybean plant according to claim 1, wherein the first promoter and the second promoter are both seed specific promoters.

5. The transformed soybean plant according to claim 1, wherein the first promoter and the second promoter are the same.

6. The transformed soybean plant according to claim 5, wherein the first promoter and the second promoter are both 7S promoters.

7. The transformed soybean plant according to claim 1, wherein the first promoter is different from the second promoter.

8. The transformed soybean plant according to claim 7, wherein the first promoter is a 7S promoter and the second promoter is a napin promoter.

9. The transformed soybean plant according to claim 1, wherein said first nucleic acid molecule is transcribed and is capable of selectively reducing the level of a transcript encoded by a FAD2-1 gene while leaving the level of a transcript encoded by a FAD2-2 gene partially unaffected.

10. The transformed soybean plant according to claim 1, wherein said first nucleic acid molecule is transcribed and is capable of selectively reducing the level of a transcript encoded by a FAD2-1 gene while leaving the level of a transcript encoded by a FAD2-2 gene substantially unaffected.

11. The transformed soybean plant according to claim 2, wherein said first nucleic acid molecule is transcribed and is capable of selectively reducing the level of a transcript encoded by a FAD2-1 gene while leaving the level of a transcript encoded by a FAD2-2 gene essentially unaffected.

12. A method of producing a soybean plant having a seed with reduced linolenic acid content comprising: transforming a soybean plant with a nucleic acid molecule that comprises
   (a) a first promoter operably linked to a first nucleic acid molecule having a first nucleic acid sequence that has 90% or greater identity to SEQ ID NO: 1 and its complement, wherein said first nucleic acid molecule is capable of suppressing endogenous expression of Fad2-1,and
   (b) a second nucleic acid molecule having a second nucleic acid sequence that has 90% or greater identity to SEQ ID NO: 14 and its complement, wherein the second nucleic. acid molecule is operably linked to the first promoter or a second promoter and capable of suppressing endogenous expression of Fad3-1; and
   growing said plant, wherein said plant produces seed with less linolenic acid than a plant having a similar genetic background but lacking said nucleic acid molecule.

13. A method of producing a soybean plant having a seed with increased oleic acid content comprising: transforming a soybean plant with a nucleic acid molecule that comprises
   (a) a first promoter operably linked to a first nucleic acid molecule having a first nucleic acid sequence that has 90% or greater identity to SEQ ID NO: 1 and complement thereof, wherein said first nucleic acid molecule is capable of suppressing endogenous expression of Fad2-1, and
   (b) a second nucleic acid molecule having a second nucleic acid sequence that has 90% or greater identity to SEQ ID NO: 14 and complements thereof, wherein the second nucleic acid molecule is operably linked to the first promoter or a second promoter and capable of suppressing endogenous expression of Fad3-1; and
   growing said plant, wherein said plant produces seed with more oleic acid than a plant having similar genetic background but lacking said nucleic acid molecule.

* * * * *

UNITED STATES PATENT AND TRADEMARK OFFICE
CERTIFICATE OF CORRECTION

PATENT NO. : 7,067,722 B2 Page 1 of 1
APPLICATION NO. : 10/176149
DATED : June 27, 2006
INVENTOR(S) : JoAnne J. Fillatti It is certified that error appears in the above-identified patent and that said Letters Patent is hereby corrected as shown below:

On the title page, col. 2, item (56) under the heading "Foreign Patent Documents" insert --WO 99/64579  12/1999--.

Col. 77, line 1, change "operable" to --operably--.

Col. 78, line 14, delete ".".

Signed and Sealed this

Twenty-first Day of November, 2006

JON W. DUDAS
*Director of the United States Patent and Trademark Office*